(12) United States Patent
Batra et al.

(10) Patent No.: US 9,102,660 B2
(45) Date of Patent: Aug. 11, 2015

(54) PROCESS OF MAKING PROSTACYCLIN COMPOUNDS WITH LINKER THIOL AND PEGYLATED FORMS

(71) Applicant: United Therapeutics Corporation, Silver Spring, MD (US)

(72) Inventors: Hitesh Batra, Herndon, VA (US); Liang Guo, Vienna, VA (US)

(73) Assignee: United Therapeutics Corporaiton, Silver Spring, MD (US)

( * ) Notice: Subject to any disclaimer, the term of this patent is extended or adjusted under 35 U.S.C. 154(b) by 0 days.

(21) Appl. No.: 14/223,034

(22) Filed: Mar. 24, 2014

(65) Prior Publication Data

US 2014/0288314 A1 Sep. 25, 2014

Related U.S. Application Data

(60) Provisional application No. 61/805,048, filed on Mar. 25, 2013.

(51) Int. Cl.
| | |
|---|---|
| C07D 405/12 | (2006.01) |
| C07D 307/93 | (2006.01) |
| C07D 207/12 | (2006.01) |
| C07C 323/40 | (2006.01) |
| C07C 319/06 | (2006.01) |
| C07D 207/416 | (2006.01) |

(52) U.S. Cl.
CPC ............ *C07D 405/12* (2013.01); *C07C 319/06* (2013.01); *C07C 323/40* (2013.01); *C07D 207/12* (2013.01); *C07D 207/416* (2013.01); *C07D 307/93* (2013.01); *C07C 2101/14* (2013.01); *C07C 2103/14* (2013.01)

(58) Field of Classification Search
None
See application file for complete search history.

(56) References Cited

U.S. PATENT DOCUMENTS

| | | | |
|---|---|---|---|
| 4,306,075 A | 12/1981 | Aristoff | |
| 5,153,222 A | 10/1992 | Tadepalli et al. | |
| 5,202,447 A | 4/1993 | Ohno et al. | |
| 5,234,953 A | 8/1993 | Crow et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,756,117 B1 | 6/2004 | Barnes | |
| 6,803,386 B2 | 10/2004 | Shorr et al. | |
| 6,809,223 B2 | 10/2004 | Moriarty et al. | |
| 7,199,157 B2 | 4/2007 | Wade et al. | |
| 7,345,181 B2 | 3/2008 | Kim et al. | |
| 7,384,978 B2 | 6/2008 | Phares et al. | |
| 7,417,070 B2 | 8/2008 | Phares et al. | |
| 7,879,909 B2 | 2/2011 | Wade et al. | |
| 7,999,007 B2 | 8/2011 | Jeffs et al. | |
| 8,232,316 B2 | 7/2012 | Phares et al. | |
| 8,242,305 B2 | 8/2012 | Batra et al. | |
| 8,252,839 B2 | 8/2012 | Phares et al. | |
| 8,349,892 B2 | 1/2013 | Phares | |
| 8,350,079 B2 | 1/2013 | Walsh | |
| 8,410,169 B2 | 4/2013 | Phares et al. | |
| 8,461,393 B2 | 6/2013 | Sharma | |
| 8,481,782 B2 | 7/2013 | Batra et al. | |
| 8,497,393 B2 | 7/2013 | Batra et al. | |
| 8,536,363 B2 | 9/2013 | Phares et al. | |
| 8,563,614 B2 | 10/2013 | Wade et al. | |
| 8,609,728 B2 | 12/2013 | Rothblatt et al. | |
| 8,653,137 B2 | 2/2014 | Jeffs et al. | |
| 8,658,694 B2 | 2/2014 | Jeffs et al. | |
| 2005/0165111 A1 | 7/2005 | Wade et al. | |
| 2008/0200449 A1 | 8/2008 | Olschewski et al. | |
| 2008/0280986 A1 | 11/2008 | Wade et al. | |
| 2009/0036465 A1 | 2/2009 | Roscigno et al. | |
| 2009/0124697 A1 | 5/2009 | Cloutier et al. | |
| 2010/0076083 A1 | 3/2010 | Olschewski et al. | |
| 2012/0190888 A1 | 7/2012 | Batra et al. | |
| 2012/0197041 A1 | 8/2012 | Batra et al. | |
| 2012/0216801 A1 | 8/2012 | Olschewski et al. | |

(Continued)

FOREIGN PATENT DOCUMENTS

| | | |
|---|---|---|
| WO | WO 00/57701 A1 | 10/2000 |
| WO | WO 2012/009816 A1 | 1/2012 |

(Continued)

OTHER PUBLICATIONS

U.S. Appl. No. 14/200,575, filed Mar. 7, 2014, Phares et al.
U.S. Appl. No. 14/202,618, filed Mar. 12, 2014, Batra et al.
Greene, TW, et al., "Protecting Groups," 1991, 1-11.

(Continued)

*Primary Examiner* — Michael Barker
(74) *Attorney, Agent, or Firm* — Foley & Lardner LLP

(57) ABSTRACT

A process provides for producing chiral prostacyclin derivatives of Formula (I)

(I)

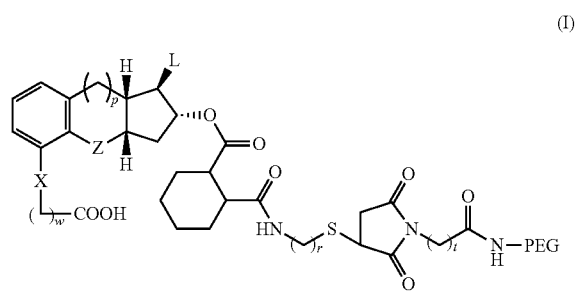

in high yield from meso anhydrides.

23 Claims, No Drawings

(56) References Cited

U.S. PATENT DOCUMENTS

2012/0323025 A1    12/2012  Sharma et al.
2013/0261187 A1    10/2013  Phares et al.

FOREIGN PATENT DOCUMENTS

WO    WO 2013/024052 A1    2/2013
WO    WO 2013/040068 A2    3/2013

OTHER PUBLICATIONS

Moriarty et al., "The Intramolecular Asymmetric Pauson-Khand Cyclization as a Novel and General Stereoselective Route to Benzindene Prostacyclins: Synthesis of UT-15 (Treprostinil)," *J. Org. Chem.* 2004, 69, 1890-1902.

Nagase et al,. "Synthesis of (+)-5,6,7-Trinor-4,8-Inter-*m*-Phenylene PGI$_2$$^1$)," Tetrahedron Letters, 1990, 31(31):4493-4494.

Sorbera et al. "UT-15. Treatment of Pulmonary Hypertension Treatment of Peripheral Vascular Disease," *Drug of the Future*, 2001, 26(4), 364-374.

PROCESS OF MAKING PROSTACYCLIN COMPOUNDS WITH LINKER THIOL AND PEGYLATED FORMS

RELATED APPLICATIONS

The present application claims priority to U.S. provisional application No. 61/805,048 filed Mar. 25, 2013, which is incorporated herein by reference in its entirety.

FIELD

The present technology relates to a process for stereoselective synthesis of prostacyclin derivatives and novel intermediate compounds useful in the process.

BACKGROUND

Prostacyclin derivatives, including treprostinil, beraprost, iloprost, and epoprostenol, are useful pharmaceutical compounds possessing activities such as platelet aggregation inhibition, gastric secretion reduction, lesion inhibition, and bronchodilation. They are useful for preventing, controlling and treating a variety of diseases and pathological conditions.

Treprostinil, the active ingredient in Remodulin®, Remodulin®, Tyvaso® and Orenitram™, was first described in U.S. Pat. No. 4,306,075. Methods of making treprostinil and other prostacyclin derivatives are described, for example, in Moriarty, et al in *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117; 8,461,393; 8,481,782; 8,242,305; 8,497,393; US patent applications nos. 2012-0190888 and 2012-0197041; PCT publication no. WO2012/009816.

Various uses and/or various forms of treprostinil are disclosed, for examples, in U.S. Pat. Nos. 5,153,222; 5,234,953; 6,521,212; 6,756,033; 6,803,386; 7,199,157; 6,054,486; 7,417,070; 7,384,978; 7,879,909; 8,563,614; 8,252,839; 8,536,363; 8,410,169; 8,232,316; 8,609,728; 8,350,079; 8,349,892; 7,999,007; 8,658,694; 8,653,137; US patent application publications nos. 2005/0165111; 2009/0036465; 2008/0200449; 2010-0076083; 2012-0216801; 2008/0280986; 2009-0124697; 2013-0261187; PCT publication no. WO00/57701; U.S. provisional application Nos. 61/791, 015 filed Mar. 15, 2013 and 61/781,303 filed Mar. 14, 2013.

Beraprost and related benzoprostacyclin analogues of the Formula (I) are disclosed in U.S. Pat. No. 5,202,447 and Tetrahedron Lett. 31, 4493 (1990). Furthermore, as described in U.S. Pat. No. 7,345,181, several synthetic methods are known to produce benzoprostacyclin analogues. Methods of making beraprost and related compounds are disclosed, for example, in US patent application publication no. 2012/0323025 and PCT publication WO2013/040068.

SUMMARY

In one aspect, a process is provided to produce a pharmaceutical compound represented by the general Formula (I) and Formula (II) in a substantially isomerically pure form. The process is completed in fewer steps than the known synthetic methods, and may be conducted to prepare commercially useful quantities. In another aspect, synthetic methods are provided for producing analogues of prostacyclin derivatives such as treprostinil and beraprost, which are stereoselective, efficient, scalable and economical. In another aspect, substantially isomerically pure compounds and intermediates are produced by the above processes. In addition, the present invention includes methods of treating pulmonary hypertension comprising administering the compounds to a subject in need thereof.

In various embodiments, a process is provided preparing compounds of Formula I and II:

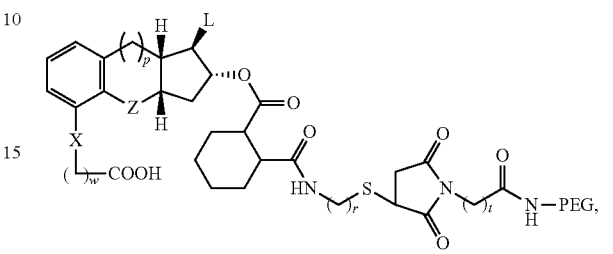

(I)

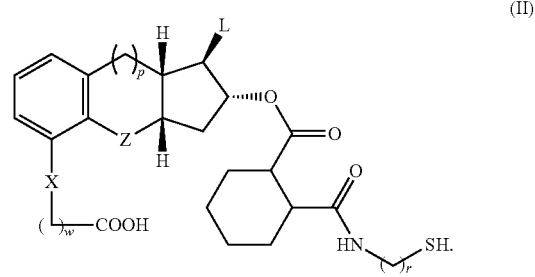

(II)

In Formulas I and II:

X is O or $CH_2$;

Z is O or $CH_2$;

L is

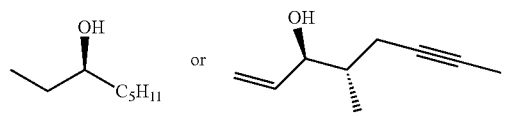

p=0 or 1;

r=1-8;

t=1, 2 or 3; and w=1, 2, or 3.

One embodiment provides a process for the preparation of a compound of Formula I, or a pharmaceutically acceptable salt thereof comprising coupling a meso anhydride of Formula III with an ester compound of Formula IV in the presence of a chiral ligand, to provide a compound of Formula V:

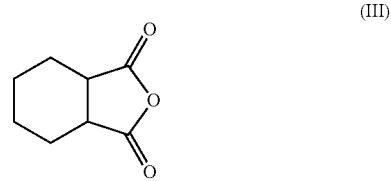

(III)

-continued

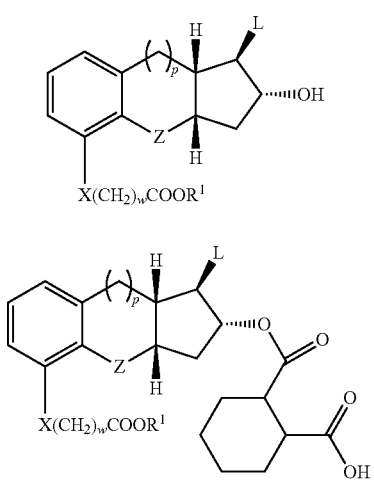
(IV)

(V)

coupling the compound of Formula V with a compound of Formula VI to form a thiol, hydrolyzing the thiol with a hydrolyzing agent to form a compound of Formula VIII;

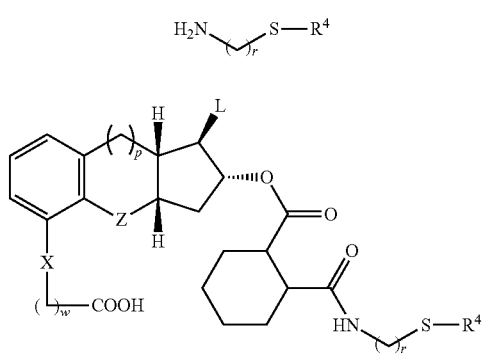
(VI)

(VIII)

deprotecting the compound of Formula VIII to form the compound of Formula II:

(II)

and coupling the compound of Formula II with a PEG-maleimide compound to form the compound of Formula I;

wherein

X is O or CH$_2$;

Z is O or CH$_2$;

L is

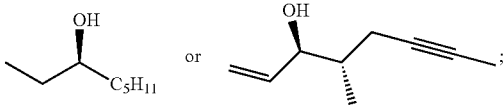

p=0 or 1;

r=1-8;

t=1, 2 or 3;

w=1, 2, or 3;

PEG is a polyethylene glycol moiety;

R$^1$ represents an acid protective group;

R$^2$ represents a hydroxyl protective group; and

R$^4$ represents a thiol protecting group.

In some embodiments, R$^1$ is a benzyl, tertiary-butyl, dimethoxy benzyl, nitrobenzyl or a dinitrobenzyl group.

In some embodiments, the chiral ligand is a quinine or quinidine derivative. In some embodiments, the quinine or quinidine derivative is hydroquinine anthraquinone-1,4-diyl diether ((DHQ)$_2$AQN), hydroquinidine anthraquinone-1,4-diyl diether ((DHQD)$_2$AQN).

In some embodiments, the hydrolyzing agent is trimethyltin hydroxide. In some embodiments, the compound of Formula VIII is deprotected using an acid. In some embodiments, the acid is trifluoroacetic acid.

Another embodiment provides a process for the preparation of a compound of Formula I, or a pharmaceutically acceptable salt thereof comprising: desymmeterizing a meso anhydride of structure III using an alcohol to provide an hemiester of Formula IX:

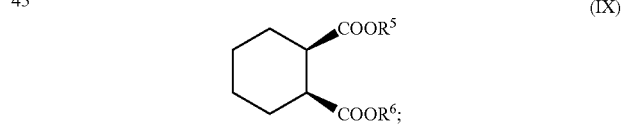
(III)

(IX)

coupling the compound of Formula IX with a compound of Formula X,

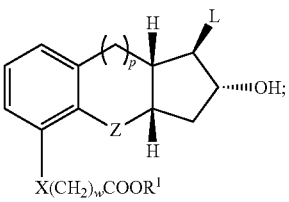
(X)

deprotecting the product of the coupling of Formula IX with Formula X, to form the compound of Formula XI:

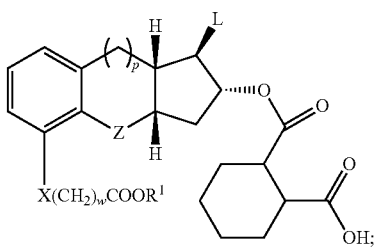
(XI)

coupling the compound of Formula XI with a compound of Formula VI, to obtain a compound of Formula VII:

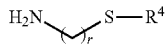
(VI)

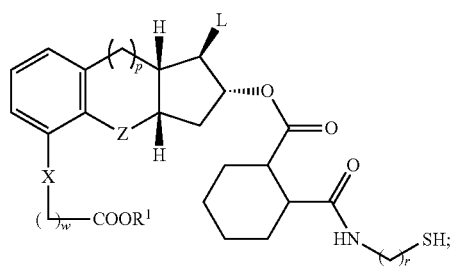
(VII)

deprotecting the compound of Formula VII to form the compound of Formula II:

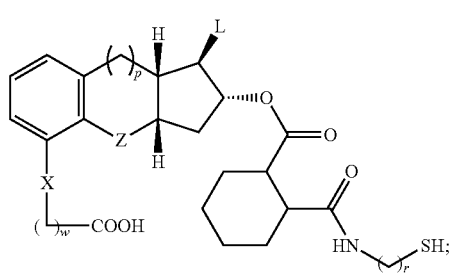
(II)

and coupling the compound of Formula II with a polyethylene glycol maleimide compound to form the compound of Formula I;

wherein Z, L, p, r, t, w, $R^1$, $R^2$ and $R^4$ are as defined herein;

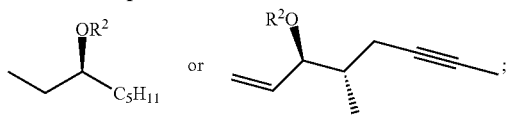

$L^1$ is and one of $R^5$ and $R^6$ represents H and the other represents a $C_{1-6}$ alkyl, allyl, or an aryl group.

In some embodiments, $R^1$ is a benzyl, tertiary-butyl, dimethoxy benzyl, nitrobenzyl or a dinitrobenzyl group.

In other embodiments, $R^2$ is a tetrahydropyranyl, benzyl, methoxybenzyl, nitrobenzyl, tertiary butyl dimethyl silyl or a tertiary methyl dimethyl silyl group.

In some embodiments, the compound of Formula VII is deprotected using an acid. In some embodiments, the acid is trifluoroacetic acid.

Yet another embodiment provides a process for the preparation of a compound of Formula I, or a pharmaceutically acceptable salt thereof comprising desymmeterizing a meso anhydride of Formula III using an alcohol to provide an hemiester of Formula IX:

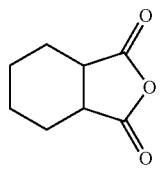
(III)

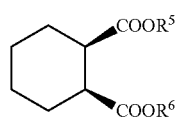
(IX)

coupling the compound of Formula IX with a compound of Formula VI, to provide a compound of Formula XII (VI)

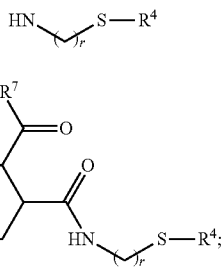

(XII)

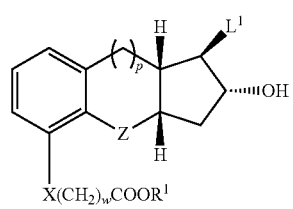

coupling the compound of Formula XII with a compound of Formula X, (X)

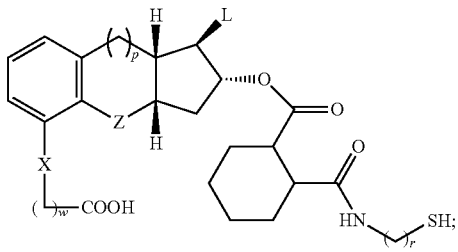

deprotecting the product of the coupling of Formula XII with Formula X, to form the compound of Formula II:

(II)

and coupling the compound of Formula II with a polyethylene glycol maleimide compound to form the compound of Formula I;

wherein X, Z, L, $L^1$, p, r, t, w, $R^1$, $R^2$ and $R^4$ are as defined herein; and $R^7$ represents an acid protective group.

In some embodiments, $R^1$ is a benzyl, tertiary-butyl, dimethoxy benzyl, nitrobenzyl or a dinitrobenzyl group. In some embodiments, $R^2$ is a tetrahydropyranyl, benzyl, methoxybenzyl, nitrobenzyl, tertiary butyl dimethyl silyl or a tertiary methyl dimethyl silyl group. In some embodiments, $R^7$ is a $C_{1-6}$ alkyl group.

In some embodiments, X is O, w is 1, r is 6; and t is 2. In other embodiments, X is $CH_2$, w is 2, r is 6 and t is 2.

In some embodiments, compounds of formulas (I), (II), (IV), (V), (VII), (VIII), (IX), (X), (XI) may be treprostinil based, i.e. having X being 0, Z being $CH_2$, w being 1, p being 1 and L being

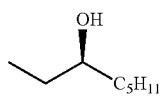

(or L' being

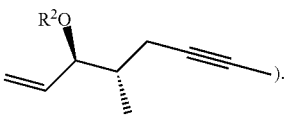

).

In some embodiments, the purity level of compound of Formula I is at least 90%, 95%, or 99%. In other embodiments, the purity level of compound of Formula II is at least 90%, 95%, or 99%. Even more preferably, the purity level of the compounds of Formula I and II is at least 99.1%, 99.2%, 99.3%, 99.4%, 99.5%, 99.6%, 99.7%, 99.8% or 99.9%.

In some embodiments, the polyethylene glycol maleimide compound is a 4-arm 20 KDa PEG maleimide.

One embodiment provides a compound of Formula IA, prepared by any of the processes described herein.

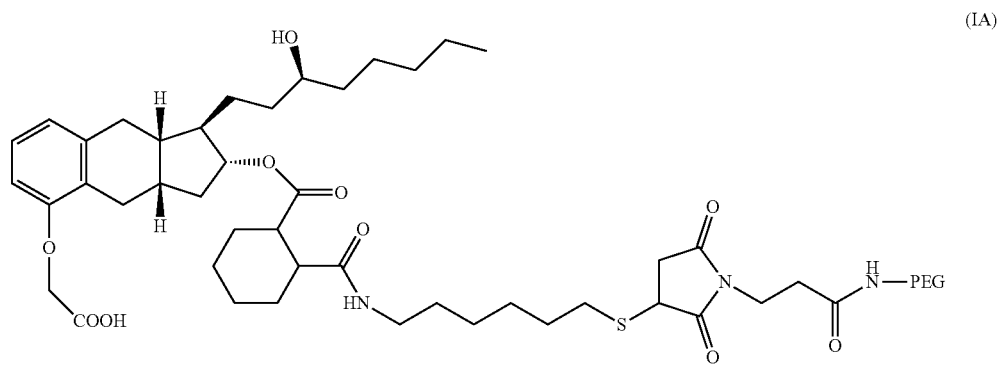

(IA)

(or L' being

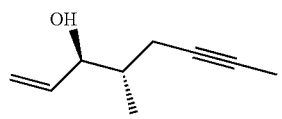

).

Yet in some embodiments, compounds of formulas (I), (II), (IV), (V), (VII), (VIII), (IX), (X), (XI) may be beraprost based, i.e. having X being $CH_2$, Z being 0, w being 2, p being 0 and L being

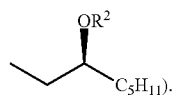

Another embodiment provides a compound of Formula IIA, prepared by any of the processes described herein.

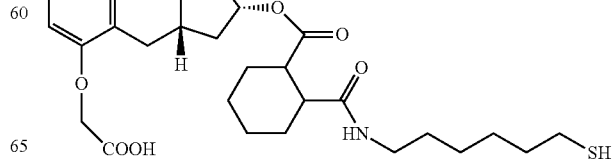

(IIA)

One embodiment provides compound of Formula IB, prepared by any of the processes described herein.

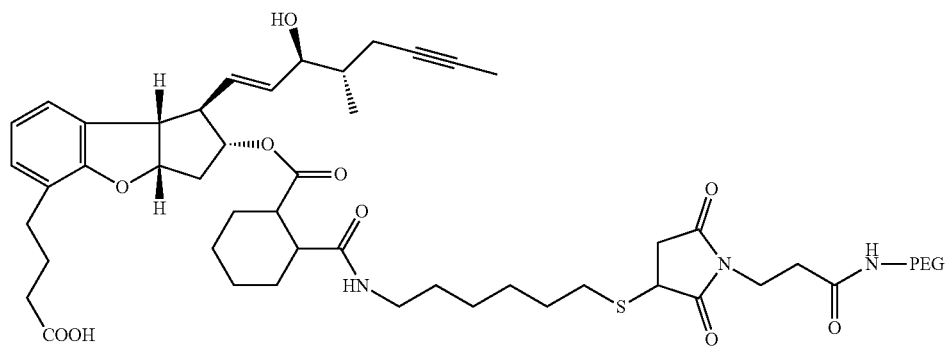

(IB)

Another embodiment provides a compound of Formula IIB, prepared by any of the processes described herein.

(IIB)

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The expression "comprising" means "including but not limited to." Thus, other non-mentioned substances, additives, carriers, or steps may be present. Unless otherwise specified, "a" or "an" means one or more.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_{m-n}$, such as $C_{1-12}$, $C_{1-8}$, or $C_{1-6}$ when used before a group refers to that group containing m to n carbon atoms.

The term "alkoxy" refers to —O-alkyl.

As used herein, "halo" or "halogen" or even "halide" can refer to fluoro, chloro, bromo, and iodo.

The term "alkyl" refers to monovalent saturated aliphatic hydrocarbyl groups having from 1 to 12 carbon atoms (i.e., $C_1$-$C_{12}$ alkyl) or 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom.

Combinations of substituents and variables are only those that result in the formation of stable compounds. The term "stable", as used herein, refers to compounds which possess stability sufficient to allow manufacture and which maintains the integrity of the compound for a sufficient period of time to be useful for the purposes detailed herein.

As used herein, the term "prodrug" means a derivative of a compound that can hydrolyze, oxidize, or otherwise react under biological conditions (in vitro or in vivo) to provide an active compound. Examples of prodrugs include, but are not limited to, derivatives of a compound that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate).

As used herein, "hydrate" is a form of a compound wherein water molecules are combined in a certain ratio as an integral part of the structure complex of the compound.

As used herein, "solvate" is a form of a compound where solvent molecules are combined in a certain ratio as an integral part of the structure complex of the compound.

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included are pharmaceutically acceptable salts or compounds of any of the Formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

As used herein, "protecting group" or "protective group" is used as known in the art and as demonstrated in Greene, *Protective Groups in Organic Synthesis*.

As used herein, "hydroxylprotective group" or "hydroxylprotecting group" refers to the generally understood definition of an alcohol or hydroxylprotecting group as defined in T. W. Greene, *Protective Groups in Organic Synthesis*, John Wiley and Sons, 1991 (hereinafter "Greene, *Protective Groups in Organic Synthesis*").

As used herein, "thiol protective group" or "thiol protecting group" refers to the generally understood definition of protection for the thiol group as defined in T. W. Greene, *Protective Groups in Organic Synthesis*, John Wiley and Sons, 1991 (hereinafter "Greene, *Protective Groups in Organic Synthesis*").

As used herein, "acid protective group" or "acid protecting group" refers to the generally understood definition of protection for the carboxylic acid group as defined in T. W. Greene, *Protective Groups in Organic Synthesis*, John Wiley and Sons, 1991 (hereinafter "Greene, *Protective Groups in Organic Synthesis*").

As used herein, "amine protective group" or "amine protecting group" refers to the generally understood definition of protection for the amino group as defined in T. W. Greene, *Protective Groups in Organic Synthesis*, John Wiley and Sons, 1991 (hereinafter "Greene, *Protective Groups in Organic Synthesis*").

As used herein, substantially pure compound or isomer refers to one isomer being 90% of the resulting isomeric mixture, or preferably 95% of the resulting isomeric mixture, or more preferably 98% of the resulting isomeric mixture, or even more preferably 99% of the resulting isomeric mixture, and most preferably above 99% of the resulting isomeric mixture.

In one aspect, processes are providing for preparing prostacyclin derivatives. Such derivatives may in some embodiments, include derivatives of Treprostinil and Beraprost. The processes also include the preparation of a number of intermediate compounds useful in the preparation of prostacyclin derivatives.

One embodiment provides processes for the preparation of a chiral linker thiol prostacyclin derivative and a PEGylated prostacyclin derivative. A chiral linker thiol is a core starting material used to prepare PEGylated prostacyclins, such as PEGylated treprostinil (PEG UT-15) and PEGylated beraprost. PEGylated prostacyclins, such as PEGylated treprostinil (PEG UT-15) and PEGylated beraprost may be used in a slow-release formulations. For example, PEG UT-15 may be used in a "slow-release" formulation of the prostacyclin analog treprostinil. Treprostinil attached to a polymeric carrier via a transient linker thiol (TransCon linker) may lead to an extended in vivo half-life after being administered to a subject, such as a human being, in need thereof. Such administering may be for example, subcutaneous injection into the body of the subject. Unmodified treprostinil is released by hydrolytic cleavage of the linker under physiological pH and temperature. Treprostinil is coupled to the linker by one of its hydroxyl groups, and the linker is attached to the PEG carrier via a thiosuccinimide group. In one embodiment, treprostinil is intended to be released from Peg UT-15 after subcutaneous injection in the patient. The process may be a much more efficient, commercially viable process to manufacture the target compounds. Pegylated beraprost may be used in a "slow-release" formulation of the prostacyclin analog beraprost. Beraprostl attached to a polymeric carrier via a transient linker thiol (TransCon linker) may lead to an extended in vivo half-life after being administered to a subject, such as a human being, in need thereof.

In some embodiments, a "slow-release" formulation of pegylated prostacyclin, such as pegylated treprostinil or pegylated beraprost, may have a release half-life of at least 12 hours, or at least 15 hours, or at least 18 hours, or at least 21 hours, or at least 24 hours, or at least 27 hours, or at least 30 hours, or at least 36 hours, or at least 42 hours, or at least 48 hours, or at least 54 hours, or at least 60 hours, or at least 72 hours, or at least 84 hours, or at least 96 hours, or at least 5 days, or at least 6 days, or at least 7 days, or at least 8 days, or at least 9 days, or at least 10 days, or at least 11 days, or at least 12 days, or at least 13 days. In some embodiments, a "slow-release" formulation of pegylated prostacyclin, such as pegylated treprostinil or pegylated beraprost, may have a release half-life in aqueous solution or buffer of at least 12 hours, or at least 15 hours, or at least 18 hours, or at least 21 hours, or at least 24 hours, or at least 27 hours, or at least 30 hours, or at least 36 hours, or at least 42 hours, or at least 48 hours, or at least 54 hours, or at least 60 hours, or at least 72 hours, or at least 84 hours, or at least 96 hours, or at least 5 days, or at least 6 days, or at least 7 days, or at least 8 days, or at least 9 days, or at least 10 days, or at least 11 days, or at least 12 days, or at least 13 days. In some embodiments, a "slow-release" formulation of pegylated prostacyclin, such as pegylated treprostinil or pegylated beraprost, may have a release half-life in plasma, which may be plasma of an mammal, such as a human being, of at least 12 hours, or at least 15 hours, or at least 18 hours, or at least 21 hours, or at least 24 hours, or at least 27 hours, or at least 30 hours, or at least 36 hours, or at least 42 hours, or at least 48 hours, or at least 54 hours, or at least 60 hours, or at least 72 hours, or at least 84 hours, or at least 96 hours, or at least 5 days, or at least 6 days, or at least 7 days, or at least 8 days, or at least 9 days, or at least 10 days, or at least 11 days, or at least 12 days, or at least 13 days.

The processes of the present disclosure may allow producing pegylated prostacyclins, such as pegylated treprostinil or pegylated beraprost, on a larger scale. For example, in some embodiments, the process of the present disclosure may allow producing of at least 5 g of pegylated prostacyclin, such as pegylated treprostinil or pegylated beraprost, or at least 10 g, or at least 20 g or at least 30 g or at least 40 g or at least 50 g or at least 60 g or at least 70 g or at least 80 g or at least 90 g or at least 100 g or at least 110 g or at least 120 g or at least 130 g or at least 140 g or at least 150 g or at least 160 g or at least 170 g or at least 180 g or at least 190 g or at least 200 g.

One embodiment provides a process for the preparation of a compound of Formula I, or a hydrate, solvate, prodrug, or pharmaceutically acceptable salt thereof.

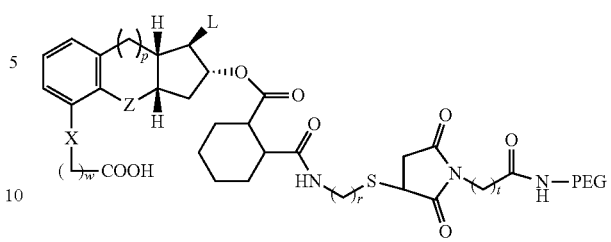

(I)

wherein
X is O or $CH_2$;
Z is O or $CH_2$;
L is

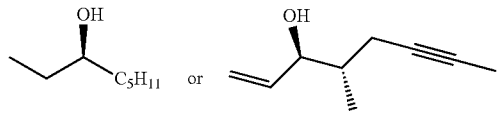

p=0 or 1;
r=1-8;
t=1, 2 or 3; and
w=1, 2, or 3.
In some embodiments, X is O, w is 1, r is 6; t is 2 and L is

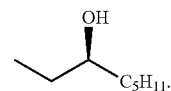

In some embodiments, X is $CH_2$, w is 2, r is 6; t is 2 and L is

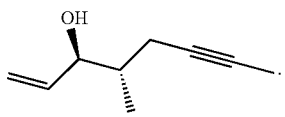

In one embodiment, the compound of Formula I has the Formula IA:

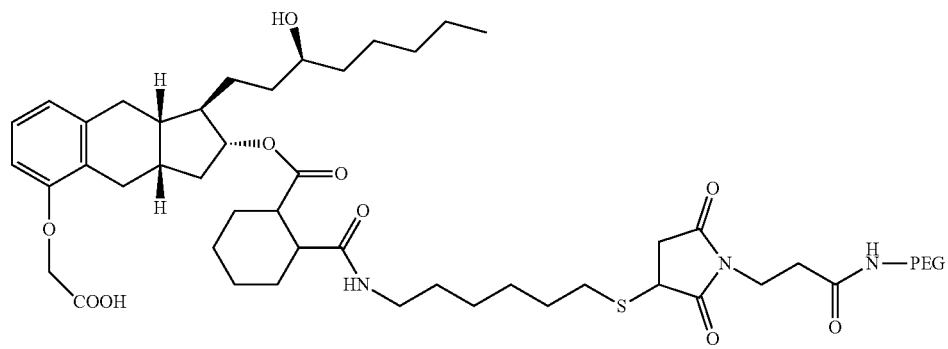

(IA)

In another embodiment, the compound of Formula I has the Formula IB:

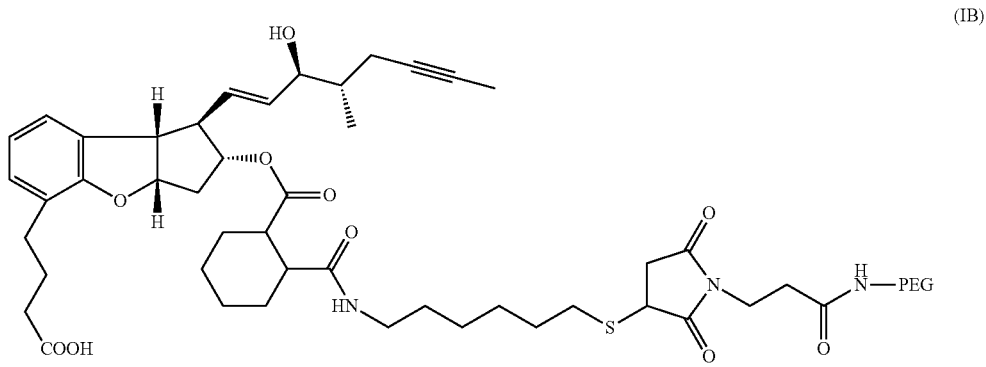

(IB)

Another embodiment provides a process for the preparation of a compound of Formula II, or a hydrate, solvate, prodrug, or pharmaceutically acceptable salt thereof

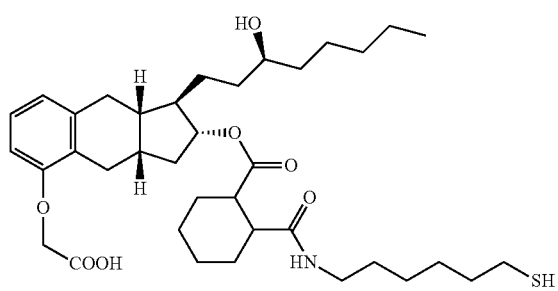

(II)

wherein Z, L, p, r, t and w are as defined herein.

In one embodiment, the compound of Formula II has the Formula IIA:

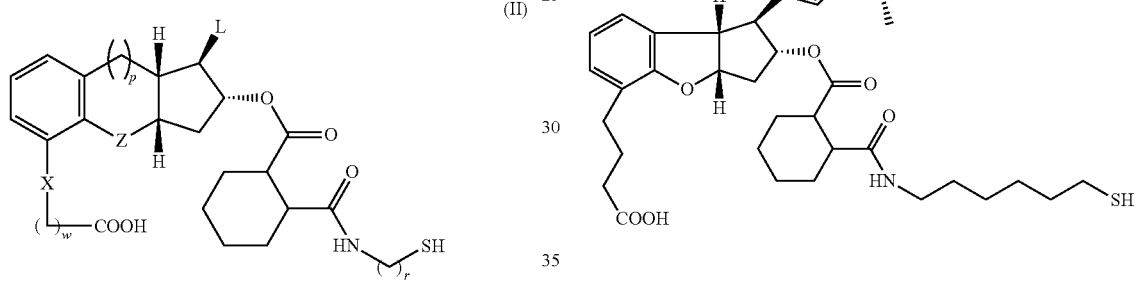

(IIA)

In another embodiment, the compound of Formula II has the Formula IIB:

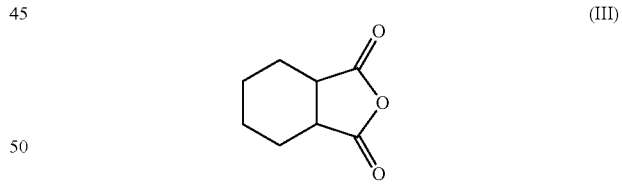

(IIB)

One embodiment provides a process for the preparation of a compound of Formula I, a hydrate, solvate, prodrug, or pharmaceutically acceptable salt thereof, starting from a meso anhydride of Formula III.

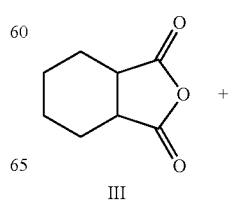

(III)

In one embodiment, the meso anhydride of Formula III can be directly coupled with an ester compound of Formula IV in the presence of a chiral ligand, to provide a compound of Formula V.

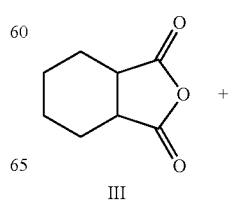 +

III

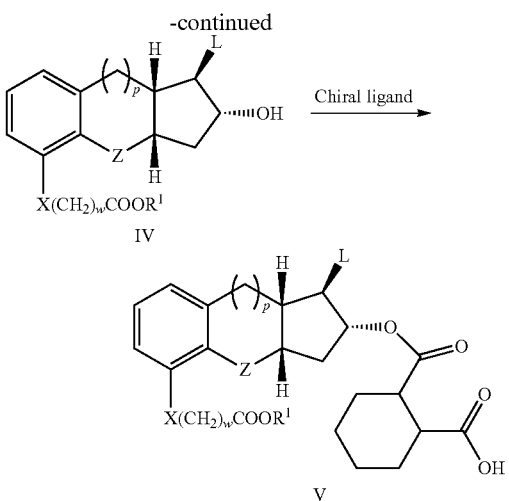

wherein L, X, Z, p, w, and $R^1$ are as defined herein.

Suitable chiral ligands include, but are not limited to, quinine, quinidine, cinchonine, cinchonidine hydroquinine, epiquinidine, epicinchonidine, epicinchonine and epiquinine, or derivatives thereof. In some embodiments, the chiral ligand is a quinine or quinidine derivative. In some embodiments, the chiral ligand is selected from hydroquinine anthraquinone-1,4-diyl diether ($(DHQ)_2AQN$), hydroquinidine anthraquinone-1,4-diyl diether ($(DHQD)_2AQN$), hydroquinine 1,4-phthalazinediyl diether ($(DHQ)_2PHAL$), hydroquinidine 1,4-phthalazinediyl diether ($(DHQD)_2PHAL$), β-isoquinidine (β-IQD), and the like. In one embodiment, the chiral ligand is $(DHQ)_2AQN$ or $(DHQD)_2AQN$.

In some embodiments, a solvent for the coupling of the meso anhydride of Formula III with the ester compound of Formula IV in the presence of a chiral compound to form the compound of formula V may be an alcohol. Suitable alcohols will be apparent to one skilled in the art and include, but are not limited to methanol, ethanol, n-propanol, isopropanol, n-butanol, isobutanol, cyclohexanol, allyl alcohol, benzyl alcohol, methoxybenzyl alcohol, nitrobenzyl alcohol, chlorobenzyl alcohol, diphenylmethanol, cyclohexylmethyl alcohol, cinnamyl alcohol, and the like. In illustrative embodiments, the alcohol is benzyl alcohol. In some embodiments, a solvent for the coupling of the meso anhydride of Formula III with the ester compound of Formula IV in the presence of a chiral agent to form the compound of formula V may be an aromatic solvent, preferably a non-polar aromatic solvent, such as toluene.

Suitable temperatures for the reaction are less than about 100° C., less than about 80° C., less than about 60° C., less than about 40° C., less than about 20° C., less than about 0° C., or any other suitable temperatures. In some embodiments, the reaction is conducted at room temperature. Suitable reaction times depend on the temperature and other conditions, and may be less than about 30 hours, less than about 20 hours, less than about 10 hours, less than about 5 hours, less than about 2 hours, less than about 1 hour, or any other suitable times. Longer times may also suitable.

In some embodiments, the coupling of the meso anhydride of Formula III with the ester compound of Formula IV in the presence of a chiral compound to form the compound of formula V may comprise first forming a salt of the chiral agent, such as quinine, and the compound of formula V, and then reacting the formed salt with an acid, such as e.g. HCl, to form the compound of formula V as an acid. In some embodiments, the salt of the chiral agent, such as quinine, and the compound of formula V may be crystallized. Such crystallization step may increase a high optical purity of the compound of formula V (as an acid). The purity of the desired stereo isomer of the compound of formula V may be at least or greater 90% or at least or greater 91% or at least or greater 92% or at least or greater 93% or at least or greater 94% or at least or greater 95% or at least or greater 96% or at least or greater 97% or at least or greater 98% or at least or greater 99% or at least or greater 99.1% or at least or greater 99.2%.

The crystallization reaction may be performed in a number solvents. For example, suitable solvents include but are not limited to, acetone, hexane, heptane, cyclohexane, acetonitrile, toluene, ethylene, ethyl acetate, methanol, ethanol, 1-propanol, 2-propanol, 1-butanol, 2-butanol, tert-butanol, ethylene glycol, dioxane, 1,2-dichloroethane, dichloromethane, dimethoxyethane, diethylene glycol, dimethyl ether, tetrahydrofuran, diisopropyl ether, methyl ethyl ketone or isobutyl methyl ketone, dimethylformamide, dimethylacetamide, MTBE or N-methylpyrrolidone, and mixtures thereof. In some embodiments, the solvent composition includes a binary solvent mixture e.g., ethyl acetate-hexane, ethyl-acetate-heptane, isopropyl alcohol heptane and the like.

Suitable acids, which may be utilized for neutralization of the salt of the chiral agent and the compound of formula V include, but are not limited to, mild acids such as dilute hydrochloric acid, sulfuric acid, and nitric acid or any mild organic acid such as acetic acid, and para-toluene sulfonic acid, or polymer based sulfonic acids such as amberlyst and the like.

The compound of Formula V can then be coupled with a compound of Formula VI, under suitable coupling conditions, to provide a compound of Formula VII

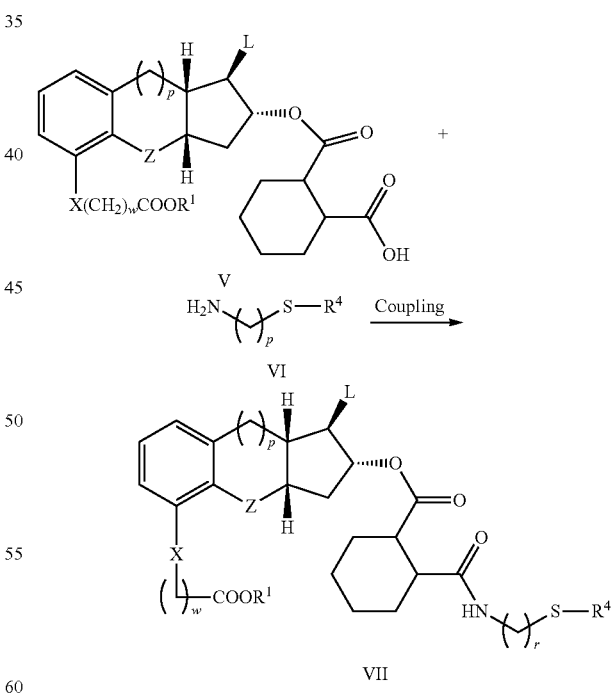

wherein L, X, Z, p, r, w, $R^1$ and $R^4$ are as defined herein.

Suitable conditions for coupling the amine of Formula VI to the carboxylic acid group of compound of Formula V will be apparent to one skilled in the art. In some embodiments, the coupling is conducted in a suitable solvent in the presence of a coupling agent. Suitable coupling agents include, but are not limited to, N-ethyl-N'-[3-(dimethylamino)propyl]-carbodiimide hydrochloride (EDC), dicyclohexylcarbodiimide (DDC), diisopropylcarbodiimide N-hydroxy benzotriazole (HOBT), 4,5-dicyanoimidazole, dicyclopentylcarbodiimide, 1-ethyl-3-(3-dimethylamino propyl)carbodiimide hydrochloride, 1,1'-carbonyldiimidazole, cyclohexylisopropyl carbodiimide (CIC), bis[[4-(2,2-dimethyl-1,3-dioxolyl)]-methyl]carbodiimide, N,N'-bis(2-oxo-3-oxazolidinyl)-phosphinic chloride (BOP-CI), an acid chloride, ethyl chloroformate, and the like.

Suitable solvents for the coupling reaction include, but are not limited to, an alcohol, e.g., methanol, ethanol, isopropyl alcohol, 1-propanol, 1-butanol, 2-butanol, a ketone, e.g., acetone, ethyl methyl ketone, methyl isobutyl ketone, a hydrocarbon, e.g., toluene, xylene, hexanes, heptanes, cyclohexane, a halogenated hydrocarbon, e.g., dichloromethane, ethylene dichloride, chloroform, an ester, e.g., ethyl acetate, n-propyl acetate, n-butyl acetate, t-butyl acetate, an ether, e.g., diethyl ether, diisopropyl ether, methyl t-butyl ether, tetrahydrofuran, dioxane, a polar aprotic solvent, e.g., N,N-dimethylformamide, N,N-dimethylacetamide, dimethylsulfoxide, sulfolane, N-methylpyrrolidone, a nitrile, e.g., acetonitrile, propionitrile, water; or mixtures thereof.

Suitable temperatures for the coupling reaction are less than about 100° C., less than about 80° C., less than about 60° C., less than about 40° C., less than about 20° C., less than about 0° C., or any other suitable temperatures. Suitable coupling reaction times depend on the temperature and other conditions, and may be less than about 30 hours, less than about 20 hours, less than about 10 hours, less than about 5 hours, less than about 2 hours, less than about 1 hour, or any other suitable times. Longer times may also suitable.

The compound of Formula VII can then be hydrolyzed with a hydrolyzing agent to form a compound of Formula VIII to remove the carboxylic acid protective group.

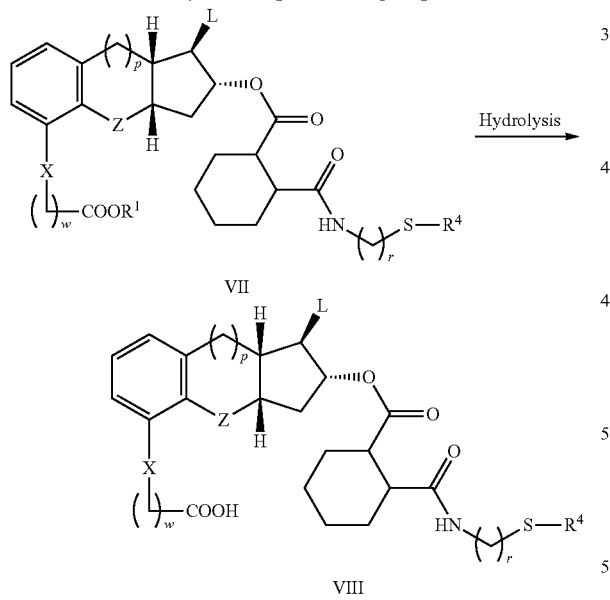

wherein L, X, Z, p, r, w, and $R^4$ are as defined herein.

Suitable carboxylic acid protective groups $R^1$ are known in the art and include the ester derivatives of a carboxylic acid group commonly employed to block or protect the carboxylic acid group while reactions are carried out on other functional groups on the compound. Exemplary carboxylic acid-protecting groups include allyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2'4,4'-tetramethoxybenzhydryl, t-butyl, t-amyl, trityl, 4-methoxytrityl, 4,4'-dimethoxytrityl, 4,4',4"-trimethoxytrityl, 2-phenyl-prop-2-yl, trimethylsilyl, t-butyldimethylsilyl, phenacyl, 2,2,2-trichloroethyl, b-(tri-methylsilyl)ethyl, b-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. In some embodiments, $R^1$ is a benzyl, tertiary-butyl, dimethoxy benzyl, nitrobenzyl or a dinitrobenzyl group.

Suitable hydrolyzing agents for removal of the carboxylic acid protective group include, but are not limited to lithium hydroxide, barium hydroxide, sodium hydroxide, potassium hydroxide, calcium hydroxide, ammonium hydroxide, sodium carbonate, potassium carbonate, trimethyltin hydroxide, tributyltin hydroxide, palladium-carbon in presence of hydrogen under basic conditions, and the like, and combinations thereof.

Suitable solvents for the hydrolysis reaction include, but are not limited to, methanol, ethanol, isopropyl alcohol, dichloromethane, 1,2-dichloroethane, chloroform, acetone, ethylmethylketone, methylisobutylketone, ethylacetate, n-propylacetate, 1,4-dioxane, n-butylacetate, t-butylacetate, diethylether, dimethylether, di-isopropylether, toluene, xylene, acetonitrile, propionitrile, methyltertiarybutylether, tetrahydrofuran, butylronitrile, or their mixtures. In some embodiments alcoholic solvents are methanol, ethanol, and isopropylalcohol are utilized with hydrolyzing agents such as barium and lithium hydroxide. In an illustrative embodiment, the compound of Formula VII is hydrolyzed using trimethyl tin in the presence of dichloroethane solvent.

Suitable temperatures for the hydrolysis reaction are less than about 100° C., less than about 80° C., less than about 60° C., less than about 40° C., less than about 20° C., less than about 0° C., or any other suitable temperatures.

The compound of Formula VIII can then be subjected to deprotection to remove the thiol protective group to form the compound of Formula II

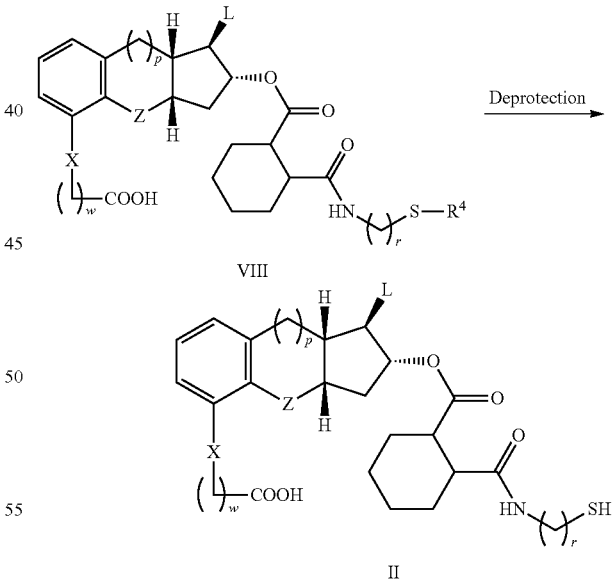

wherein L, X, Z, p, r, w, and $R^4$ are as defined herein.

Suitable thiol protecting groups are known in the art and include benzyl, 4-methoxybenzyl (MBzl), triphenylmethyl (trityl), methoxytrityl, tert-butyl (tBu), t-butylthiol, acetyl, 3-nitro-2-pyridinesulphenyl and acetamidomethyl (Acm).

The thiol protective group $R^4$ may be removed selectively using deprotecting agents known in the art. In some embodiments, the thiol protecting group may be removed with an acid, e.g., mineral acids such as hydrochloric acid, and aqueous or anhydrous organic acids, e.g., carboxylic acids such as acetic acid, TFA, or sulphonic acids such as methanesulphonic acid. In some embodiments, the thiol protecting group may be removed by oxidative cleavage, for example by treatment with mercury (II), iodine, silver (I) or thallium (III). In some embodiments, the acid may be used along with an oxidizing agent such as DMSO, tetramethylenesulphoxide, potassium superoxide, nickel peroxide, sodium trithiocarbonate, triphenylbismuth carbonate and the like. In some embodiments, the thiol protective group is a trityl group. In some embodiments, the trityl group may be removed using trifluoroacetic acid. In some embodiments, the trityl group may be removed using 1,1,1,3,3,3-Hexafluoroisopropyl Acrylate (HFIPA) and triethylsilane (TES).

The compound of Formula II may be coupled with a suitable polyethylene glycol maleimide compound to form the compound of Formula I.

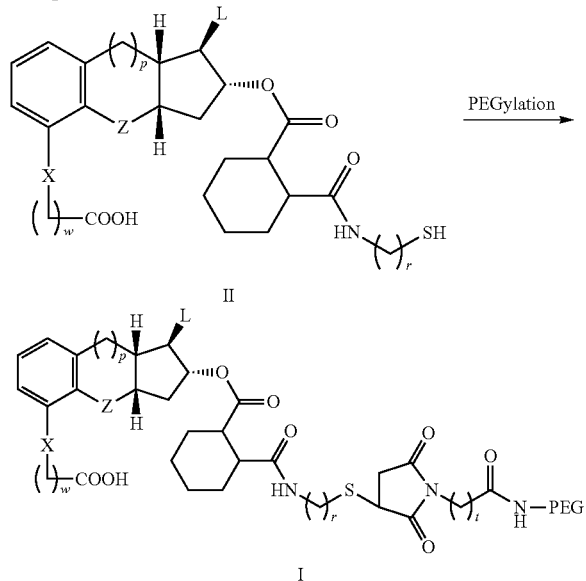

wherein L, Z, p, r, t, and w are as defined herein.

In one embodiment, the polyethylene glycol maleimide compound has the following structure The PEG moiety (polyethylene glyclol moiety) includes preferred polyethylene glycols having an average molecular weight of from about 200 to about 200,000. In some embodiments, the polyethylene glycol has an average molecular weight of from about 200 to about 80000. In some embodiments, the polyethylene glycols are PEG 1500, PEG 4000, PEG 5000, PEG 8000, PEG 10,000, PEG 15,000, PEG 20,000 and PEG 25,000. In some embodiments, the polyethylene glycol is PEG 20,000.

The linker thiol may be contacted with the PEG compound in a suitable solvent at the suitable pH. The pH can be maintained at the desired value using a suitable buffer. For example, the pH can be maintained at about 6.5 using a phosphate buffer. Suitable solvents for the reaction include, but are not limited to, acetone, hexane, heptane, cyclohexane, acetonitrile, toluene, ethylene, ethyl acetate, methanol, ethanol, 1-propanol, 2-propanol, 1-butanol, 2-butanol, tert-butanol, ethylene glycol, dioxane, 1,2-dichloroethane, dichloromethane, dimethoxyethane, diethylene glycol, dimethyl ether, tetrahydrofuran, diisopropyl ether, methyl ethyl ketone or isobutyl methyl ketone, dimethylformamide, dimethylacetamide or N-methylpyrrolidone, and mixtures thereof. In some embodiments, the solvent composition includes a binary solvent mixture e.g., acetone-hexane, ethyl acetate-hexane, acetone-water, water-octane, ethanol-water, hexane-cyclohexane, hexane-ethanol, chloroform-hexane, diethyl ether-water, ethanol-methanol, water-dichloromethane, and the like.

In other embodiments, the meso anhydride of Formula III can be desymmeterized into chiral hemiesters using chiral ligands in the presence of suitable alcohols described herein.

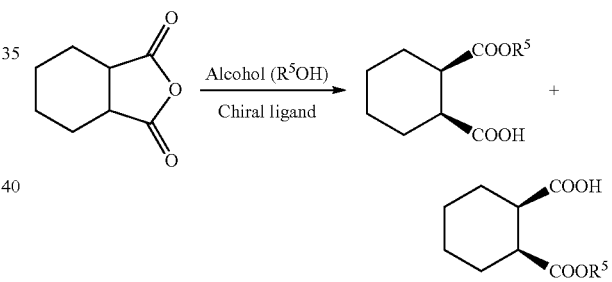

wherein $R^5$ is $C_{1-6}$ alkyl, allyl, or an aryl group.

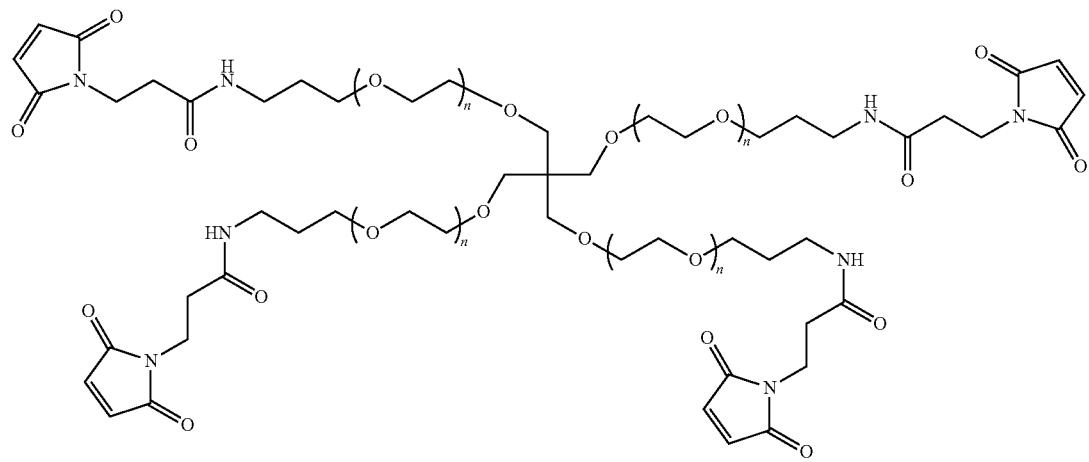

In another embodiment, the meso anhydride of Formula III can be desymmeterized in two steps. The meso-anhydride can first be treated with a chiral ligand, in the presence of a suitable alcohol such as those described above, to produce chiral hemiesters as their respective amine salts. The amine salts can then be crystallized in a suitable solvent composition, followed by neutralization with mild acid to obtain both the chiral hemiesters.

greater than 99.4%, at least or greater than 99.5%. In some embodiments, the hemiesters produced by the present methods are substantially pure. In other embodiments, the hemiesters produced by the present methods are greater than about 99% pure.

The hemiester of Formula IX can be coupled with a compound of Formula X under suitable coupling conditions.

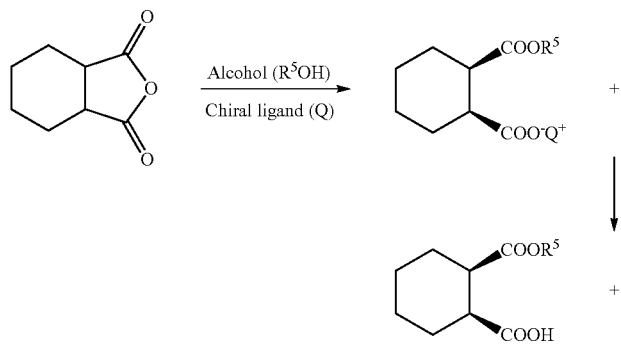

wherein $R^5$ is $C_{1-6}$ alkyl, allyl, or an aryl group.

Suitable chiral ligands and alcohols for asymmetric monoesterification will be apparent to one skilled in the art and are as described herein. In some embodiments, the chiral ligand is a quinine or a quinidine derivative. In some embodiments, the alcohol is benzyl alcohol.

Suitable solvent composition utilized for crystallization of the amine salt include, but are not limited to, acetone, hexane, heptane, cyclohexane, acetonitrile, toluene, ethylene, ethyl acetate, methanol, ethanol, 1-propanol, 2-propanol, 1-butanol, 2-butanol, tert-butanol, ethylene glycol, dioxane, 1,2-dichloroethane, dichloromethane, dimethoxyethane, diethylene glycol, dimethyl ether, tetrahydrofuran, diisopropyl ether, methyl ethyl ketone or isobutyl methyl ketone, methyl tertiary butyl ether (MTBE), dimethylformamide, dimethylacetamide or N-methylpyrrolidone, and mixtures thereof. In some embodiments, the solvent composition includes a binary solvent mixture e.g., acetone-hexane, ethyl acetate-hexane, acetone-water, isopropyl alcohol:MTBE, water-octane, ethanol-water, hexane-cyclohexane, hexane-ethanol, chloroform-hexane, diethyl ether-water, ethanol-methanol, water-dichloromethane, and the like.

Suitable acids utilized for neutralization of the amine salt will be apparent to one skilled in the art and include, but are not limited to, mild acids such as dilute hydrochloric acid, sulfuric acid, and nitric acid or any mild organic acid such as acetic acid, and para-toluene sulfonic acid, or polymer based sulfonic acids such as amberlyst and the like.

Using the methods described above, the hemiesters are obtained in high optical purity, e.g., at least or greater than 90%, at least or greater than 91%, at least or greater than 92%, at least or greater than 93%, at least or greater than 94%, at least or greater than 95% or at least or greater than 96%, at least or greater than 97%, at least or greater than 98%, at least or greater than 99%, at least or greater than 99.1%, at least or greater than 99.2%, at least or greater than 99.3%, at least or

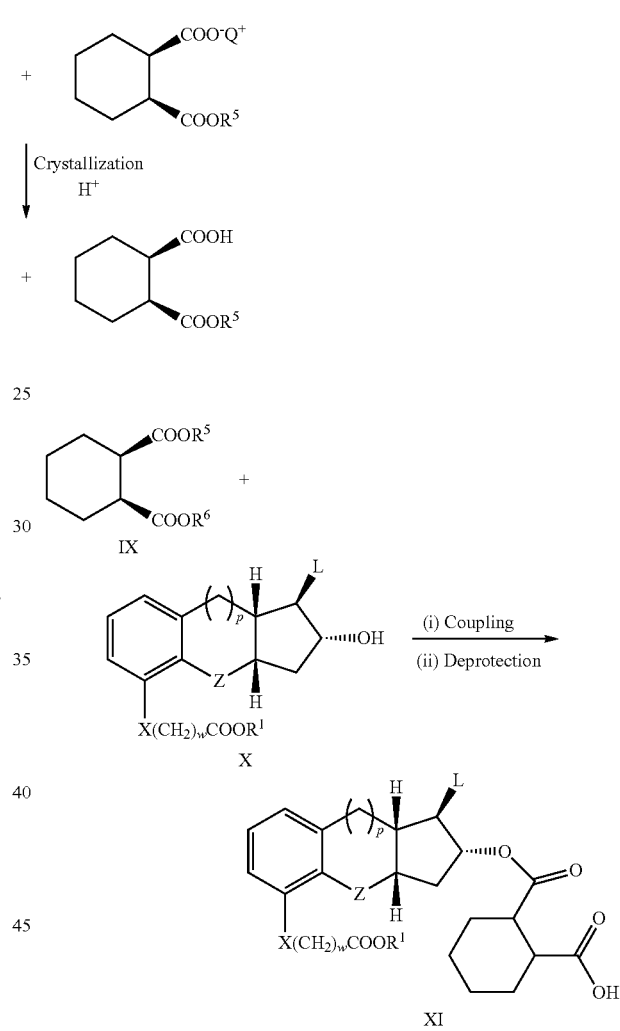

wherein $L^1$, X, Z, p, w, $R^1$, $R^5$ and $R^6$ are as defined herein.

Suitable conditions for coupling a carboxylic acid 1x with an alcohol X are known in the art. Suitable agents include esterification agents such as lewis or bronstead acids, or coupling agents such as EDC or DCC, optionally in the presence of a catalyst such as 4-dimethylaminopyridine.

The carboxylic acid group on the cyclohexane containing side chain ($COOR^5$ or $COOR^6$) can be selectively deprotected using methods known in the art and described herein. For example deprotecting agents for removal of the carboxylic acid protective group include, but are not limited to lithium hydroxide, barium hydroxide, sodium hydroxide, potassium hydroxide, calcium hydroxide, ammonium hydroxide, sodium carbonate, potassium carbonate, trimethyltin hydroxide, tributyltin hydroxide, palladium-carbon in presence of hydrogen under basic conditions, and the like, and combinations thereof.

Suitable hydroxylprotecting groups $R^2$, in the linker $L^1$, are known in the art and include, but are not limited to methyl, t-butyl, tetrahydropyranyl, benzyl, methoxybenzyl, nitrobenzyl, tertiary butyl dimethyl silyl, tertiary methyl dimethyl silyl group, methoxymethyl, methoxyethoxymethyl, allyl, trityl, ethoxyethyl, 1-methyl-1-methoxyethyl, tetrahydropyranyl, or tetrahydrothiopyranyl group. In one embodiment the hydrocxy protecting group is tetrahydropyranyl (THP). In some embodiments, the hydroxylprotecting group may be cleaved under coupling conditions. In other embodiments, the hydroxyl protecting group is cleaved under suitable conditions, such as those described herein. For example, the hydroxylprotecting group may be cleaved using a catalytic amount of an acid such as p-toluenesulfonic acid.

The compound of Formula XI can then be coupled with a compound of Formula VI to provide a compound of Formula VII.

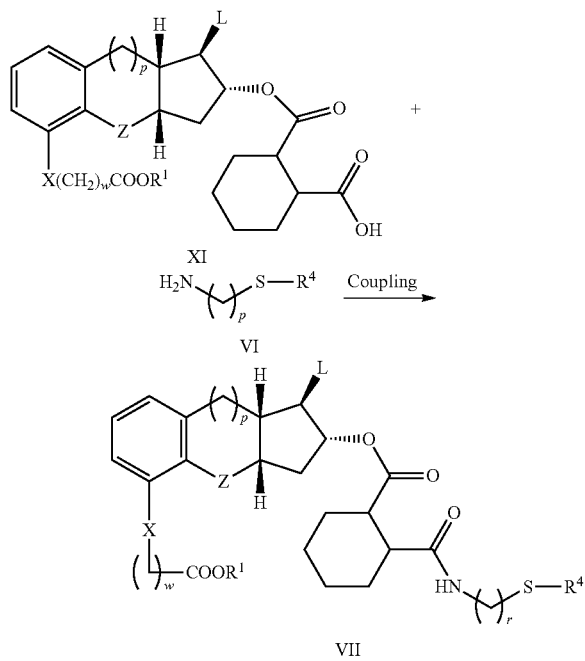

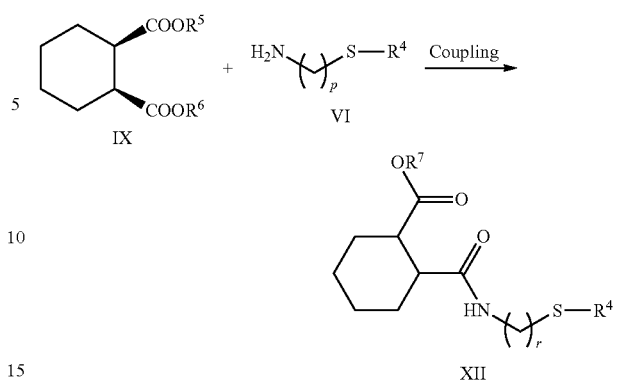

wherein $L^1$, Z, p, r, w, $R^4$, $R^5$ and $R^6$ are as defined herein, and $R^7$ is an acid protective group.

Suitable conditions for coupling the amine of Formula VI to the carboxylic acid group of compound of Formula IX will be apparent to one skilled in the art and are described herein.

In the compound of Formula XII, wherein $R^7$ is an acid protective group. Suitable acid protective groups are as described herein. In some embodiments, $R^7$ is a $C_{1-6}$ alkyl group.

The compound of Formula XII can then be coupled a compound of Formula X, followed by deprotection with catalyst to form the compound of Formula II. The compound of Formula II can further be coupled with a polyethylene glycol maleimide compound, as described herein, to provide the compound of Formula I.

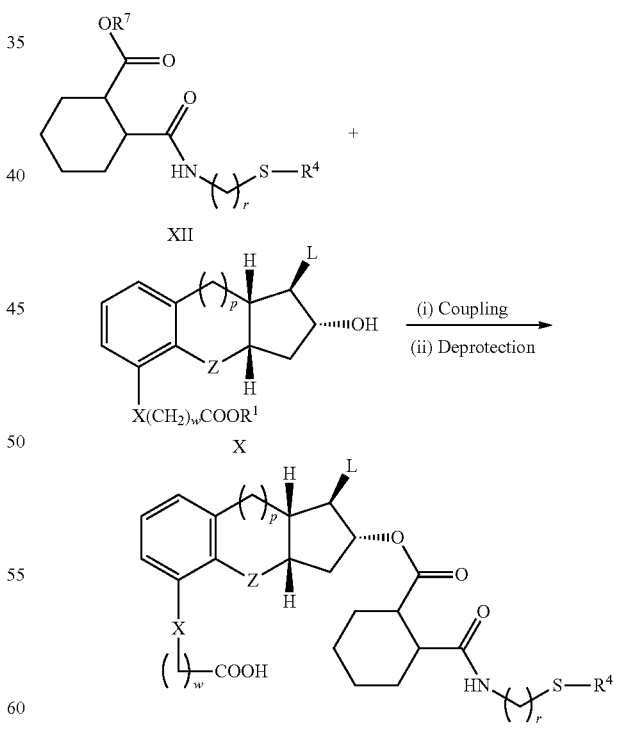

wherein L, $L^1$, X, Z, p, r, w, $R^4$, $R^5$, $R^6$ and $R^7$ are as defined herein.

wherein $L^1$, X, Z, p, r, w, $R^1$, and $R^4$ are as defined herein.

Suitable coupling conditions will be apparent to one skilled in the art and are described herein for coupling of compound of Formula V with compound of Formula VI.

The compound of Formula VII is subjected to deprotection of the carboxylic acid protecting group and the thiol protecting group, to provide a compound of Formula II. Both protecting groups can be cleaved in a single step using a strong acid, such as e.g., trifluoroacetic acid. Alternatively, the carboxylic acid protecting group is cleaved first, followed by the removal of the thiol protecting group using conditions described herein.

The compound of Formula II can further be coupled with a polyethylene glycol maleimide compound, as described herein, to provide the compound of Formula I.

In an alternate embodiment, the hemiester of Formula IX can be coupled with a compound of Formula VI, under suitable coupling conditions to provide a compound of Formula XII Suitable conditions for coupling a carboxylic acid with an alcohol are known in the art. Suitable agents include esterification agents such as lewis or bronstead acids, or coupling agents such as EDC or DCC, optionally in the presence of a catalyst such as 4-dimethylaminopyridine.

Suitable conditions for removal of carboxylic acid protective group $R^1$ are as described herein. Hydroxylprotecting group $R^2$ can be removed by acid or base catalysed hydrolysis or catalytic hydrogenolysis. For example, tetrahydropyarnyl (THP) ether protecting group may be removed, for example, by acid hydrolysis, silyl ethers may require hydrogen fluoride or tetrabutylammonium fluoride to be cleaved and benzyl ether protecting group may be removed, for example, by hydrogenolysis.

In one aspect, a substantially pure compound of Formula I, II, IA, IB, IIA, IIB, V, VII, VIII, IX, X or XI is produced by the processes described herein. The compounds have both high chemical purity and high optical purity. In some embodiments the purity of compound of Formula I is at least 90%, 95%, 97%, 99% or greater than 99%. In other embodiments, the purity of compound of Formula II is at least 90%, 95%, 97%, 99% or greater than 99%.

The processes provide advantages in large-scale synthesis over the existing methods. For example, existing synthetic processes to prepare PEG UT-15 involve extensive chiral separation of the desired linker and delivers an overall poor yield of the final product.

The present processes provide a facile, stereoselective synthesis of the PEGYlated prostacyclin derivatives, e.g., PEG UT-15 in good yield without the need for expensive chiral separations. Further since the chromatographic purification of intermediates and final products is eliminated, thus the required amount of flammable solvents and waste generated, as well as the production cost, are greatly reduced. Furthermore, the salt formation methods utilized in the present processes is a much easier operation than column chromatography. The products of the processes have higher purity; e.g., the present processes provide a single isomer of the linker thiol having an optical purity greater than 99% by HPLC. Therefore, a process is provided that is more economical, safer, faster, greener, easier to operate, and provides higher purity.

Another embodiment provides a process for preparing the amine compound of Formula VI.

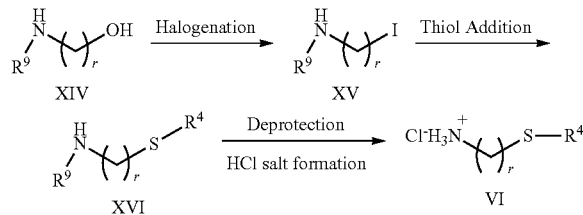

wherein r and $R^4$ are as described herein, Y is a halogen and $R^9$ is an amino protecting group.

A protected amino alcohol of Formula XIV can be halogenated under suitable conditions, to yield compound of Formula XV. In some embodiments Y is F, Cl, Br or I. In some embodiments Y is I.

Suitable halogenation conditions include e.g., reaction of compound XIV with iodine or bromine in presence of triphenylphosphine and imidazole, reaction of compound XIV with in-situ chlorophosphonium ions prepared by the reaction of carbon tetrachloride or hexachloroacetone, reaction of compound XIV with chlorodiphenylphosphine, imidazole and halogen, and the like.

The halogenated compound XV can be reacted with a suitable thiol protecting compound, such as those described herein, to yield a thiol protected compound XVI. For example, the halogenated compound XV can be reacted with triphenylmethanethiol in presence of base potassium carbonate or 1,8-Diazabicyclo[5.4.0]undec-7-ene (DBU) in the presence of a suitable solvent such as acetonitrile or dimethyl formamide, respectively. Deprotection of the amino protecting group under suitable conditions, followed by treatment with an acid, e.g. hydrochloric acid, will provide the acid salt of amine compound VI.

Suitable amino protecting compounds are known in the art. Exemplary amino protecting groups include, but are not limited to tosylate (Tos), benzyloxycarbonyl (Cbz), t-butyloxycarbonyl (Boc), acetate, and trifluoroacetate groups. Depending on the protecting group used, the amino protecting group can be cleaved under acidic or basic conditions. For example, the trifluoroacetate protecting group can be cleaved using a base, e.g., potassium carbonate.

The process for preparing the amine compound of Formula VI described herein is cleaner and more efficient than the known methods. Advantageous of the process include circumventing the use of carcinogenic compounds such as hydrazine hydrate and the avoiding the use of column chromatography or repeated trituration to obtain pure amine.

Synthetic Methods

Certain methods for making the compounds described herein are also provided. The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

The following abbreviations are used in the description and/or appended claims, and they have the following meanings:

"HPLC" means high performance liquid chromatography.
"TFA" means trifluoroacetic acid.
"THP" means tetrahydropyranyl.
"PEG" means polyethylene glycol.
"(DHQ)$_2$AQN" means Hydroquinine anthraquinone-1,4-diyl diether
"(DHQD)$_2$AQN" means Hydroquinidine (anthraquinone-1,4-diyl) diether Illustrative and non-limiting methods for synthesizing a compound of Formula (I), are schematically shown below.

General Method I-Stereospecific/Enatioselective Synthesis of Pegylated Prostacyclin Derivatives from Meso Anhydrides Scheme 1 demonstrates the preparation of an acid intermediate 11 from meso-anhydride 7. The meso-anhydride 7 was subjected to desymmetrization using various treprostinil esters 8, in presence of different chiral ligands particularly quinine 9 to obtain quinine salt of salt of acid 10. A significant difference in the reactivity of various esters of treprostinil was observed. Further, the selectivity also varied depending on the substituent. Of the various esters tested 8a-f, benzyl ester of treprostinil 8a was observed to have the better selectivity compared to other esters. The quinine salt of acid 10 neutralized to obtain acid intermediate 11. The acid intermediate can be carried as such for subsequent steps, or can be purified via salt formation and neutralization methodology.

Scheme 1: Direct Meso-Anhydride Opening with Treprostinil Alcohol

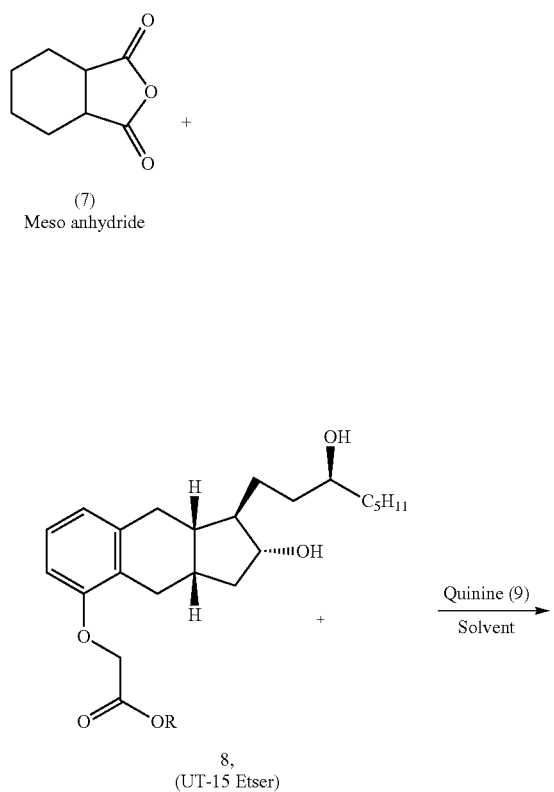

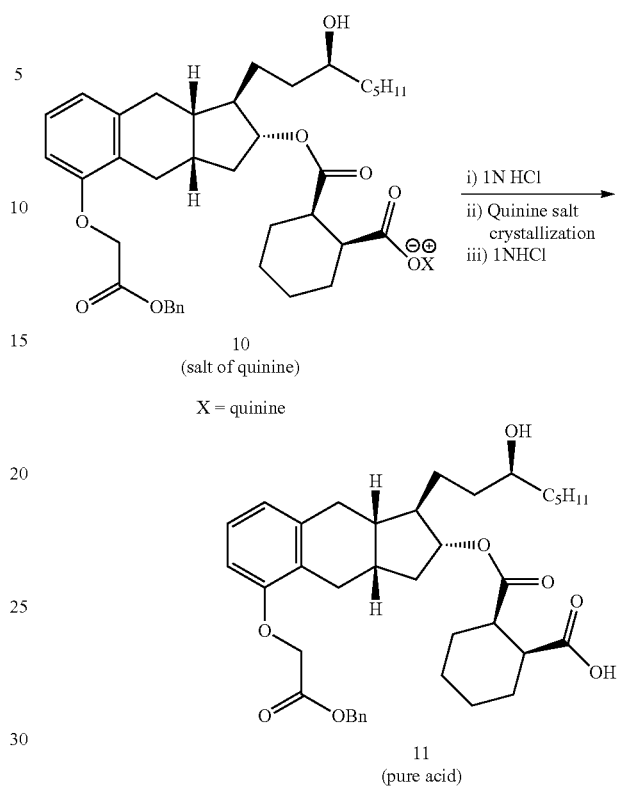

Scheme 2 demonstrates the synthesis of linker thiol 5 from acid intermediate 11. The acid intermediate 11 was subjected to amine side chain 12 coupling to obtain the linker amide 13. This linker amide 13 was subjected to hydrolysis of benzyl ester under various conditions, e.g. barium hydroxide, lithium hydroxide and PdC/H$_2$/K$_2$CO$_3$, in order to cleave the benzyl group on UT-15 moiety of amide 13. However, the reactions either lead to the formation of some by-product or no reaction was observed, likely due to the presence of sulfur in the form of trityl group.

The amide intermediate 13 was selectively hydrolyzed to acid 14 without affecting the UT-15 ester linkage at the cyclohexane moiety, by employing a very mild and selective hydrolysis of benzyl ester using trimethyltin hydroxide in 1,2-dichloroethane. The acid intermediate 14 was treated with TFA leading to cleavage of the trityl group of the amine side chain to yield linker thiol 5. The linker thiol was confirmed by HPLC and NMR data.

Scheme 2: Direct Meso-Anhydride Opening with Treprostinil Ester Alcohol

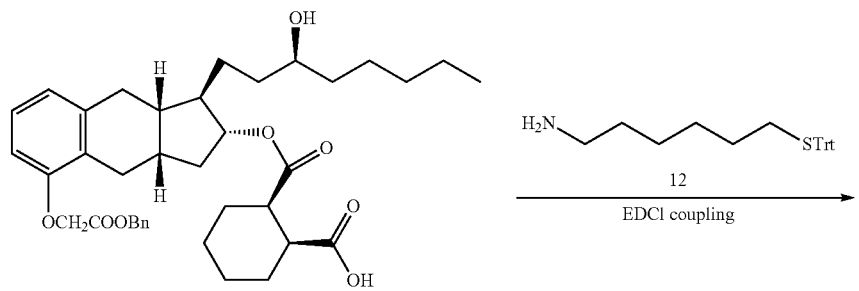

-continued
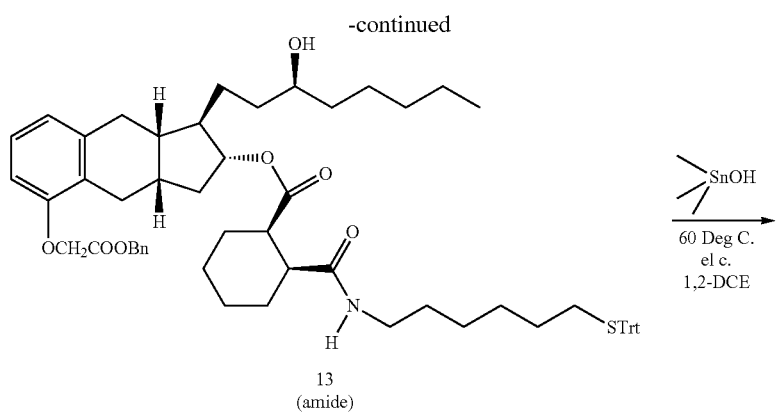
13
(amide)
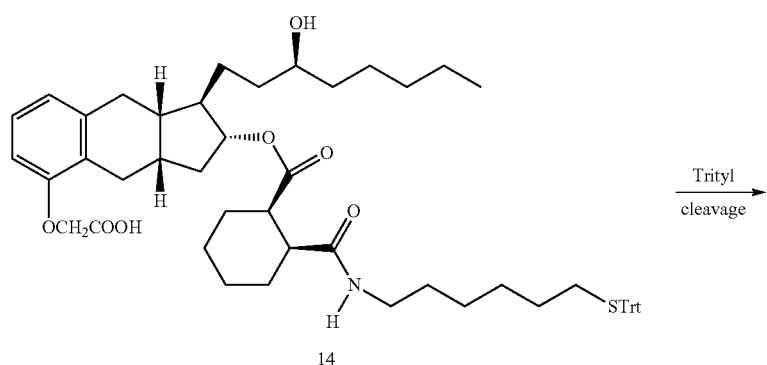
14
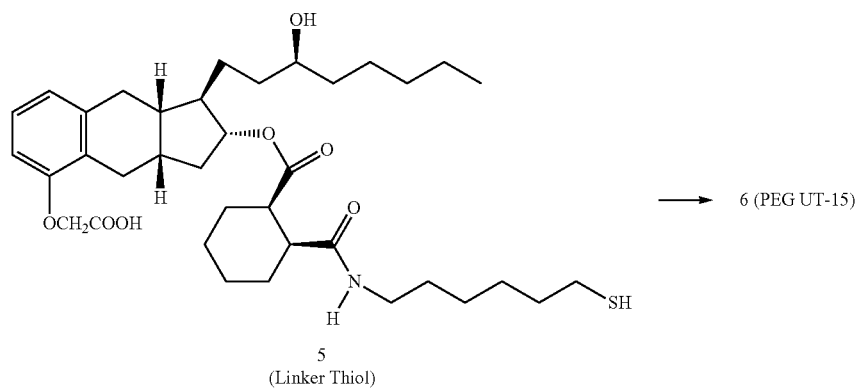
5
(Linker Thiol)
As depicted in Scheme 3, the linker thiol 5 was subjected to coupling with 4 arm 20K Da PEG maleimide to obtain PEG-UT-15 or Transcon PEG Treprostinil (6).

Scheme 3: PEGylation of thiol liker to PEG-UT-15

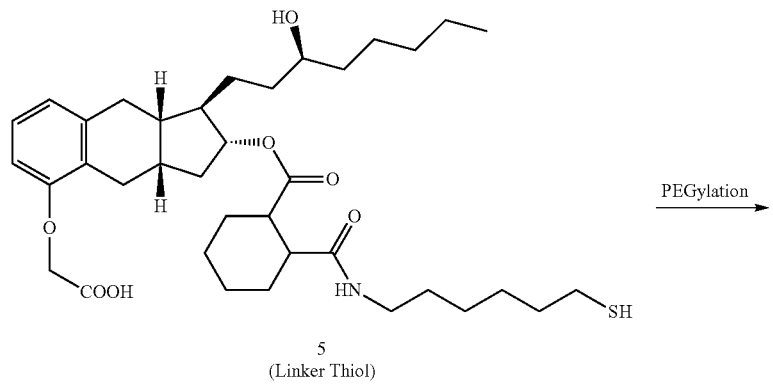

5
(Linker Thiol)

PEGylation →

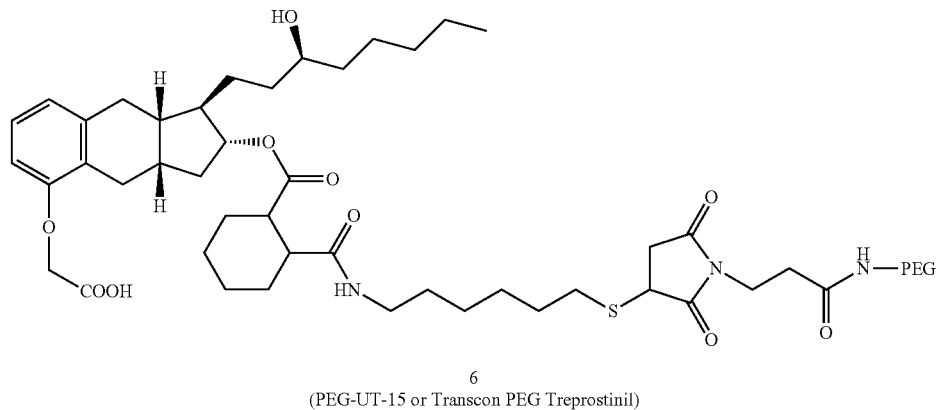

6
(PEG-UT-15 or Transcon PEG Treprostinil)

General Method II-Stereospecific/Enatioselective Synthesis of Pegylated Prostacyclin Derivatives via Chiral Hemiesters Scheme 4 demonstrates the preparation of chiral hemiesters from readily available achiral meso anhydride. The meso-anhydride 7, was directly desymmeterized to a chiral hemiesters using various alcohols to obtained hemiesters 15 and 16. In another embodiment, the achiral meso-anhydride 7 was treated with quinine and quinidine based ligands (DHQ)$_2$AQN and (DHQD)$_2$AQN in the presence of alcohols, e.g. benzyl alcohol, and desymmeterized to a chiral benzyl hemiesters 19 and 20, in optical purity ranging from 91% to 99% (purity by HPLC). The hemiesters were further purified via diastereomeric salt crystallization using quinine as chiral amine. In another embodiment, the meso-anhydride 7, was treated with quinine and quinidine in presence of benzyl alcohol and chiral benzyl hemiesters were obtained as their respective amine salts (17 and 18). The amine salts were crystallized in binary solvent mixture (acetone:hexanes or ethyl acetate:hexane) followed by neutralization with mild acid (such as dilute hydrochloric acid, sulfuric acid, and nitric acid or any mild organic acid such as acetic acid, and para-toluene sulfonic acid, or polymer based sulfonic acids such as amberlyst etc.) to obtain both the chiral benzyl esters 19 and 20 in >99% chiral purity.

Scheme 4: General Route on Desymmetrization of Meso-Anydride with Alcohols to Chiral Hemiesters

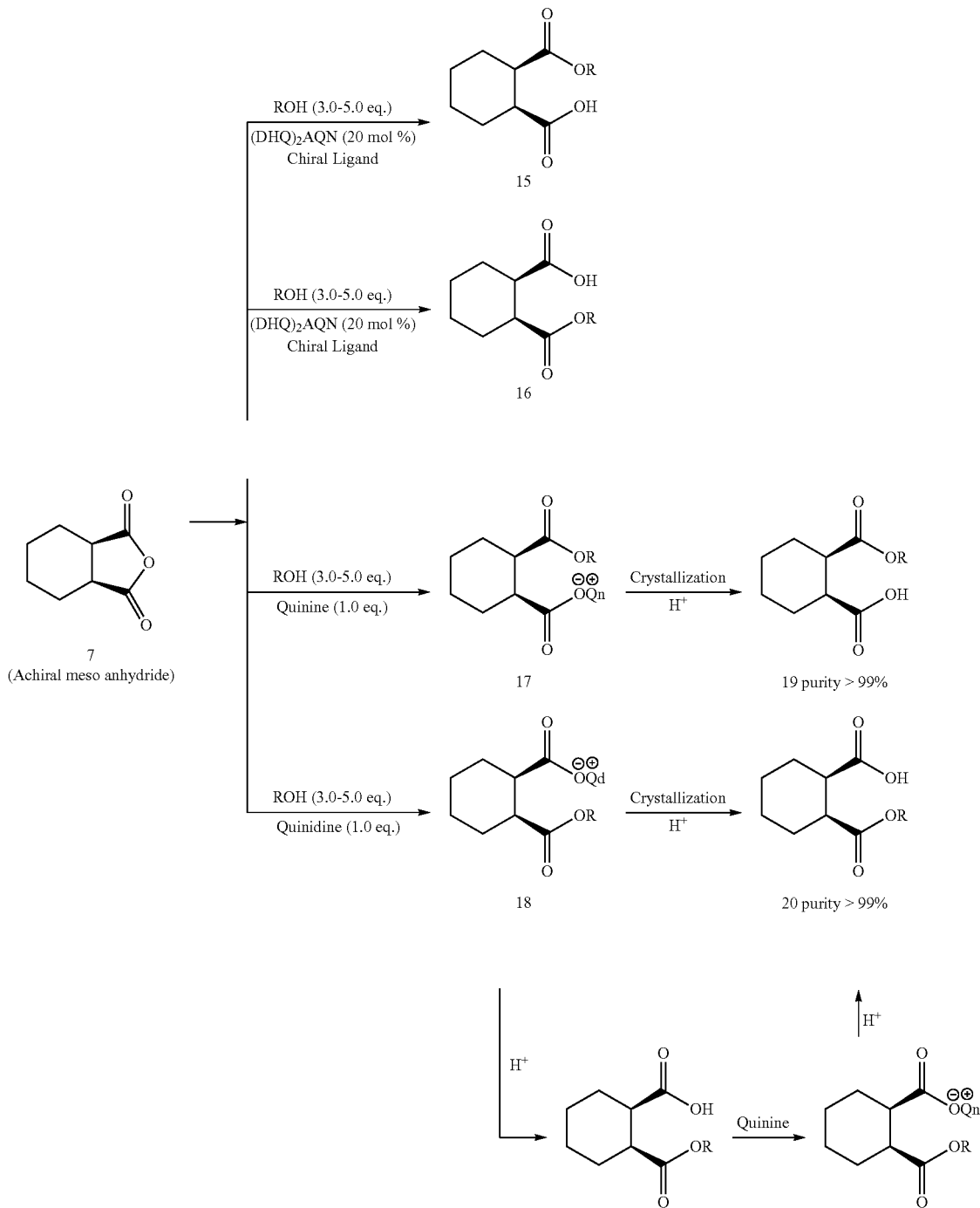

Note = Qn = Quinine
Qd = Quinidine

Scheme 5 demonstrates the two pathways for the preparation of chiral linker thiol 5 from chiral hemiesters prepared in Scheme 4. Using chiral hemiesters 19 and 20 as starting materials, there are two possible pathways to obtain the chiral linker thiol 5, having the desired stereochemical configuration. In pathway 1, the chiral benzyl hemiester 19 was coupled with amine to obtain linker amide 21. The linker amide intermediate 21 was subjected to debenzylation reaction under various reaction conditions, followed by coupling with treprostinil component to obtain protected linker thiol 23, which is deprotected to provide the linker thiol 5. In pathway 2, the chiral acid 20 is coupled with treprostinil component to obtain ester intermediate of general structure 22, which was subsequently converted first to the protected linker thiol and then the linker thiol 5, through a series of reactions depicted in Scheme 6.

Scheme 5: Pathways to Make Coupled Linker

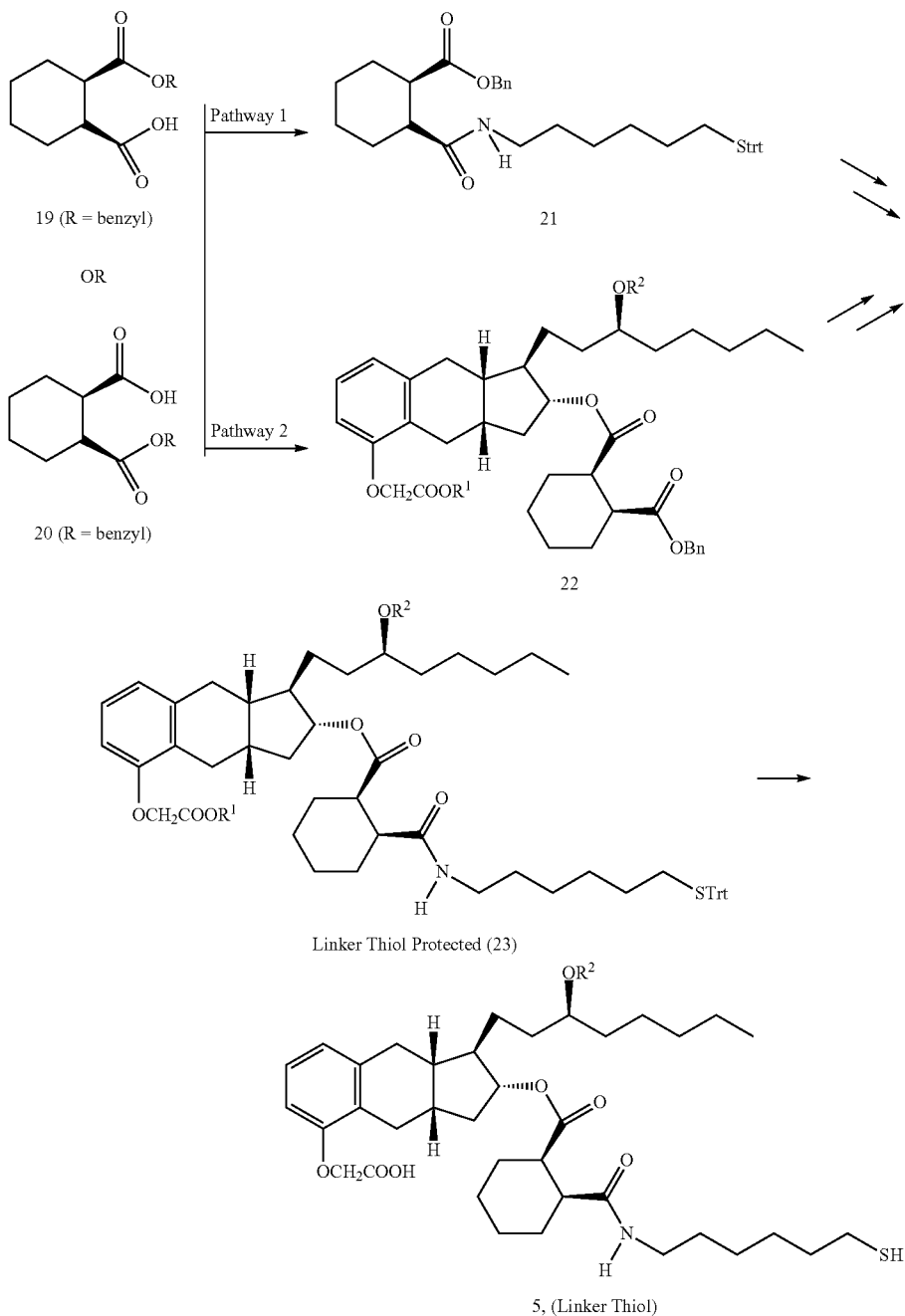

As depicted below in Scheme 6, tert.-butyl ester of treprostinil 24 was coupled with chiral hemiester 20 to obtain the protected benzyl ester intermediate 25 which upon debenzylation using Pd/C catalyst yielded the acid intermediate 26. During the debenzylation step, THP cleavage of the side chain protected alcohol was observed due to the inherent acidic nature of the molecule having a free carboxylic acid functional group. In a few experiments some uncleaved THP intermediate 27 was observed and mixture of 26 and 27 was obtained. In such cases, the mixture was stirred with catalytic amount of para-toluenesulfonic acid to cleave the THP group to yield the acid intermediate 26. If desired, this THP cleavage could be prevented by adding catalytic amount of base such sodium bicarbonate. The acid intermediate 26 was subsequently coupled with amine side chain 12 to obtain the desired protected linker intermediate 28, which was subjected to deprotection of trityl and tert-butyl groups using trifluoroacteic acid or by a two step process to remove the t-butyl group first by using acidic reagents such as polymer bound acids, silica gel etc. followed by TFA cleavage of trityl group to finally yield the chiral linker thiol 5. Analytical data was collected and HPLC as well as NMR data was compared with the reference marker sample obtained from Ascendis Pharma A/S to confirm the formation of the desired linker thiol 5. The data was found to be in agreement with the desired structure of linker thiol 5. The process was scaled-up on a 5 g scale. The linker thiol 5 was then subjected to final coupling with 4 arm 20K Da PEG maleimide to obtain PEG-UT-15 (6).
Scheme 6: Coupling via Treprostinil Moiety to obtain Linker
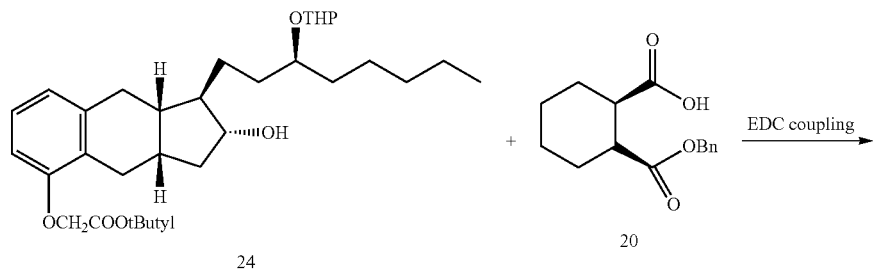
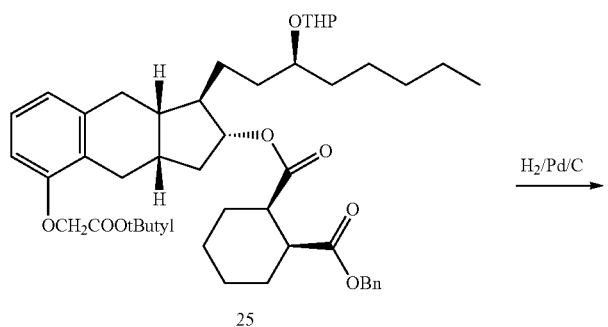
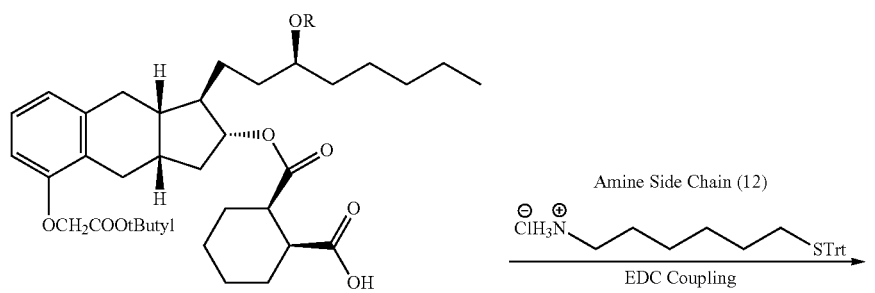
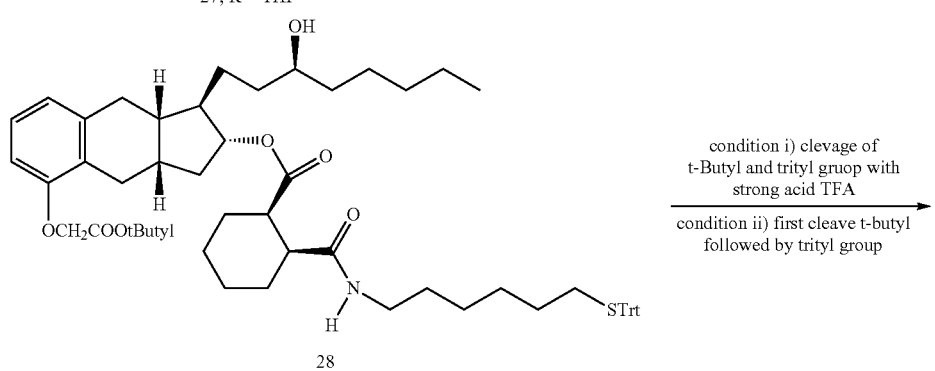

-continued

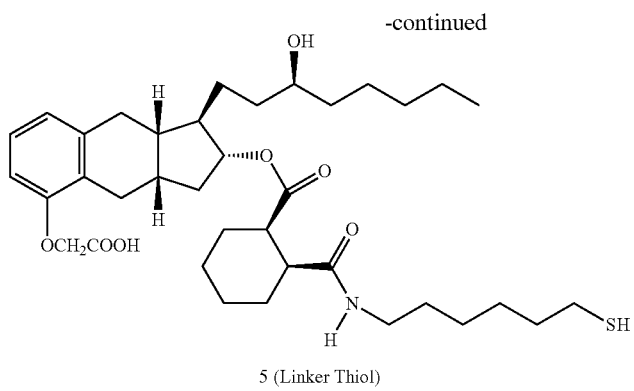

5 (Linker Thiol)

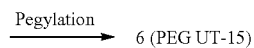

6 (PEG UT-15)

General Method III—Stereospecific/Enatioselective Synthesis of Pegylated Prostacyclin Derivatives via Diastereomeric Salt Crystallization of Hemiesters As depicted in Scheme 7, the meso anhydride 7 was treated with various alcohols such as methyl, benzyl and allyl alcohol to obtain a racemic mix of hemiesters (29 and 30; R=methyl). Various diastereomeric salt crystallization methods were also screened using chiral amines such as quinine, quinidine, and naphtahyl amine etc. It was observed that amongst the tested group of amines, quinine provided the best diastereoselectivity in producing a single diastereomeric salt 33 of the desired hemiester 29 with 99% purity. All the results were confirmed by ¹HNMR data. Once the diastereomeric quinine salt was obtained, it was converted to required chiral hemiester (29; R=Me) by simple neutralization with 1N HCl. The hemiester so obtained was carried forward for the synthesis of linker amide. The process was scaled-up on 25 g scale.

Scheme 7: Preparation of chiral hemiester via diastereomeric salt crystallization

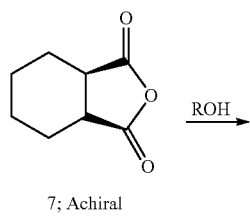

7; Achiral

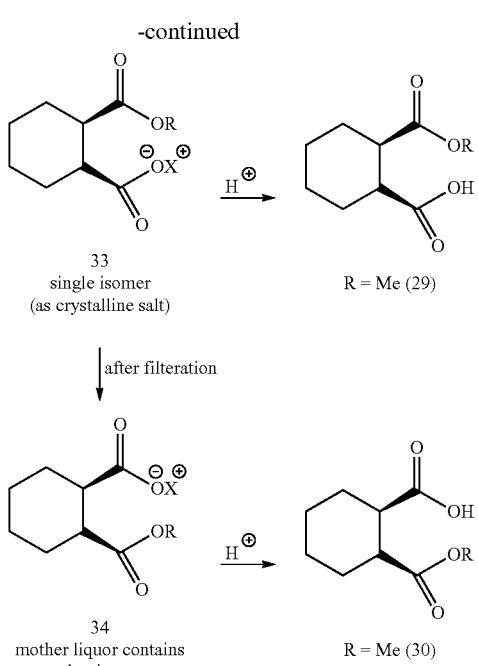

X = quinine

As depicted in Scheme 8, chiral hemiester 29 and amine 12 were coupled to obtain chiral linker amide 35 in quantitative yield. ¹H NMR data revealed the formation of the required linker in amide 35.

Scheme 8: Coupling of Amine with Acid to Obtain Linker

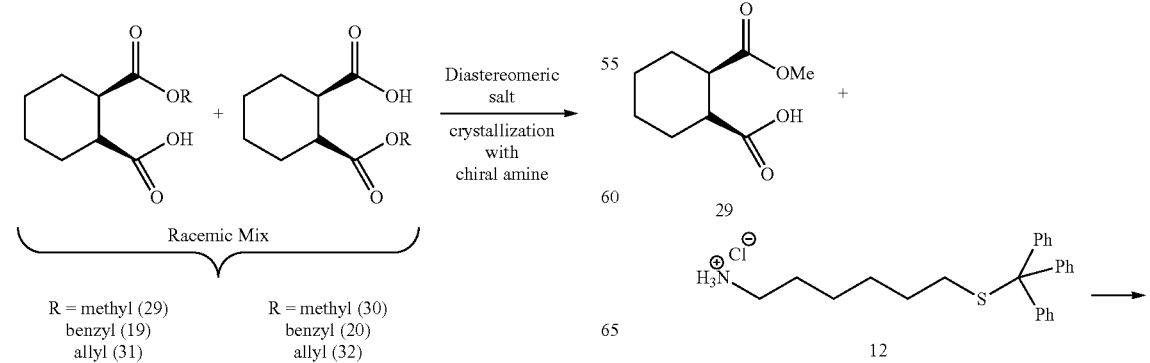

-continued

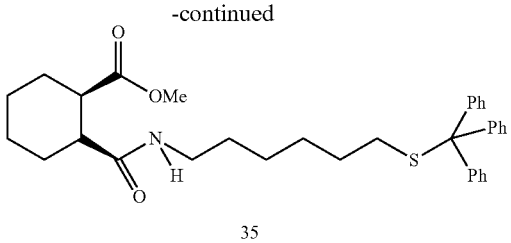
35

As depicted in Scheme 9, the chiral linker amide 35, obtained in Scheme 7, can be hydrolyzed to obtain the desired chiral cyclohexane amide linker 36, which can be subsequently coupled with treprostinil component 37 leading to the formation of linker thiol 5. The linker thiol 5 can then be subjected to final coupling with 4 arm 20K Da PEG maleimide to obtain PEG-UT-15 (6).

Scheme 9: Coupling of Linker With Treprostinil Moiety

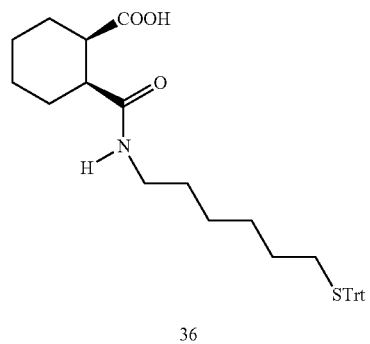
36

+

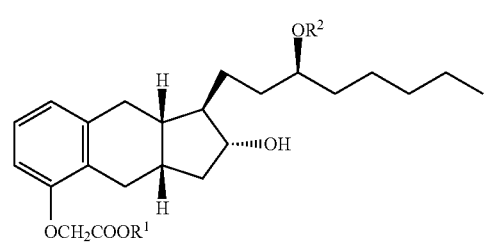
37

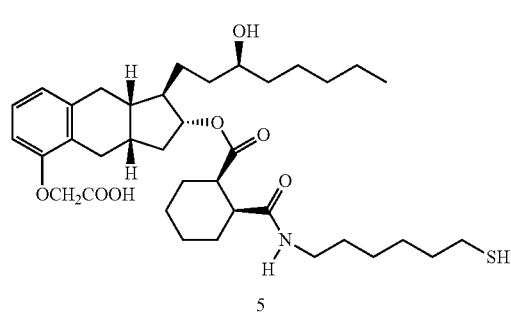
5
Penultimate Intermediate 6 (PEG UT15)

General Method IV—Synthesis of Amine Side Chain

Scheme 10 demonstrates a new synthetic route for synthesizing the amine side chain 12. Protected amino alcohol compound 41 was reacted with iodine in presence of triphenylphosphine and imidazole to yield compound 42. Iodo compound 42 was reacted with triphenylmethanethiol in presence of base potassium carbonate or DBU to yield compound 43. Deprotection of the trifluoro acetamide 43 using potassium carbonate yielded the amine side chain as a free base which was converted to hydrochloric acid salt using hydrochloric acid 12.

Scheme 10: Amine side chain using trifluoroacetamide protected amino hexanol

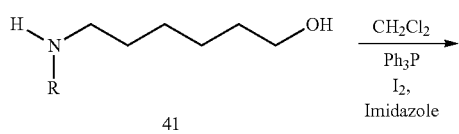
41

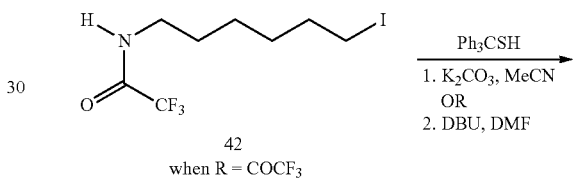
42
when R = COCF$_3$

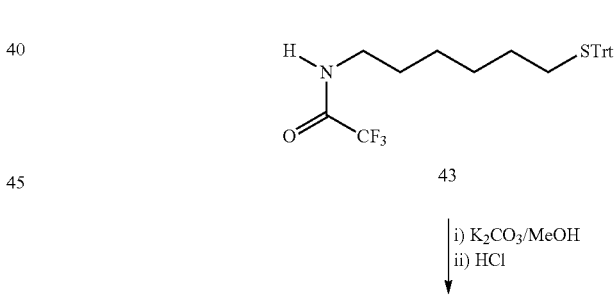
43 i) K$_2$CO$_3$/MeOH
ii) HCl

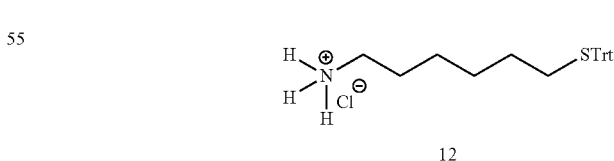
12

General Method V—Synthesis of Isomer of Linker Thiol

Scheme 11 depicts the synthesis of isomer of linker thiol 47 as analytical marker to check the purity of the desired isomer of linker thiol 5. A HPLC comparison of both the isomers was used to determine the purity of desired linker thiol 5 and any presence of unwanted isomer 47.

Scheme 11: Synthesis of isomer of linker thiol
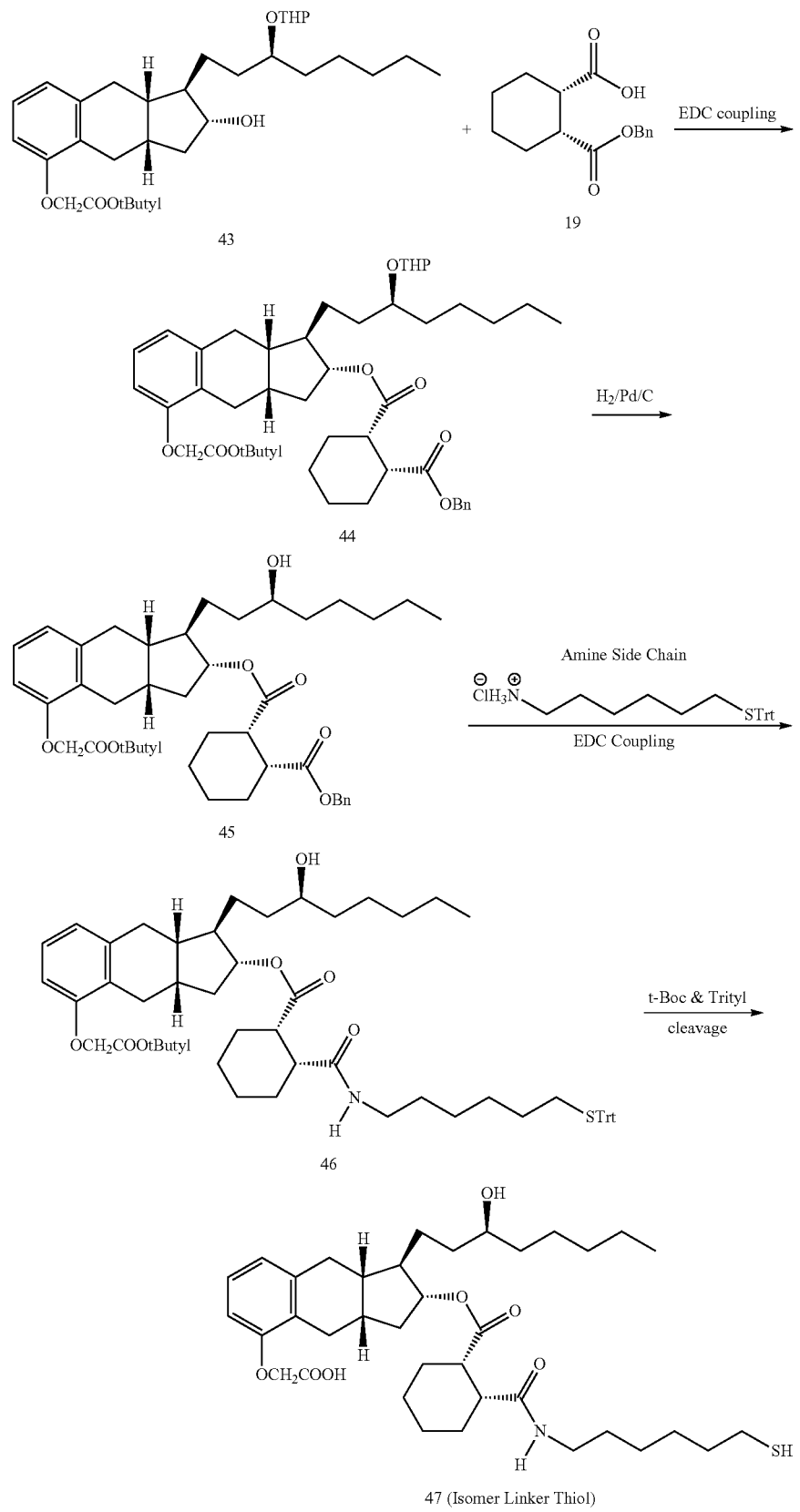

The present invention, thus generally described, will be understood more readily by reference to the following examples, which are provided by way of illustration and are not intended to be limiting of the present invention.

EXAMPLES

Example 1

Stereospecific/Enatioselective Synthesis of Pegylated Treprostinil Derivatives from Meso Anhydrides

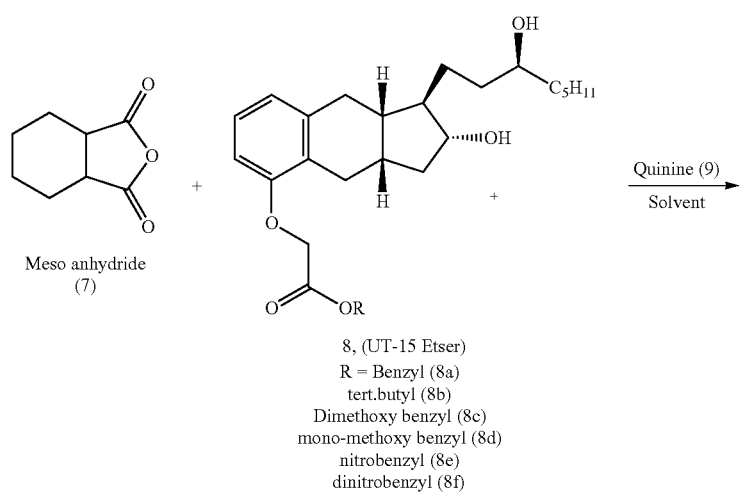

8, (UT-15 Etser)
R = Benzyl (8a)
tert.butyl (8b)
Dimethoxy benzyl (8c)
mono-methoxy benzyl (8d)
nitrobenzyl (8e)
dinitrobenzyl (8f)

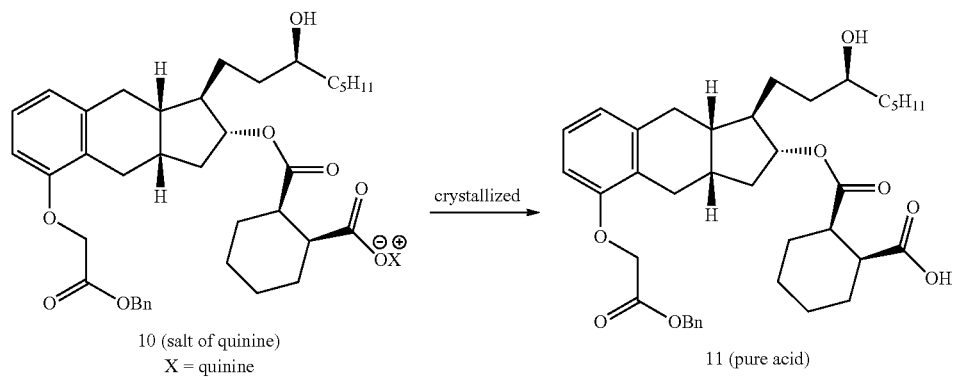

10 (salt of quinine)
X = quinine 11 (pure acid)

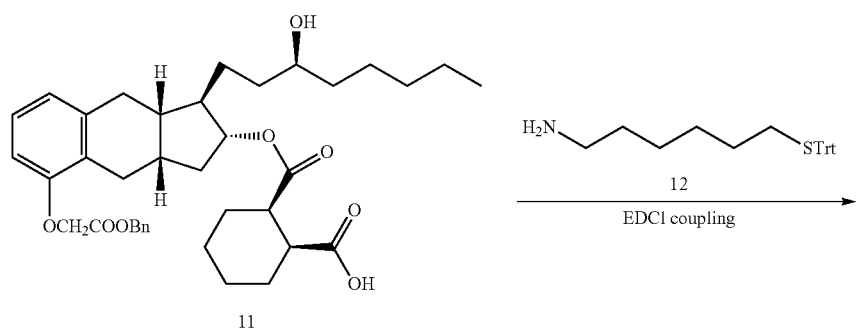

11

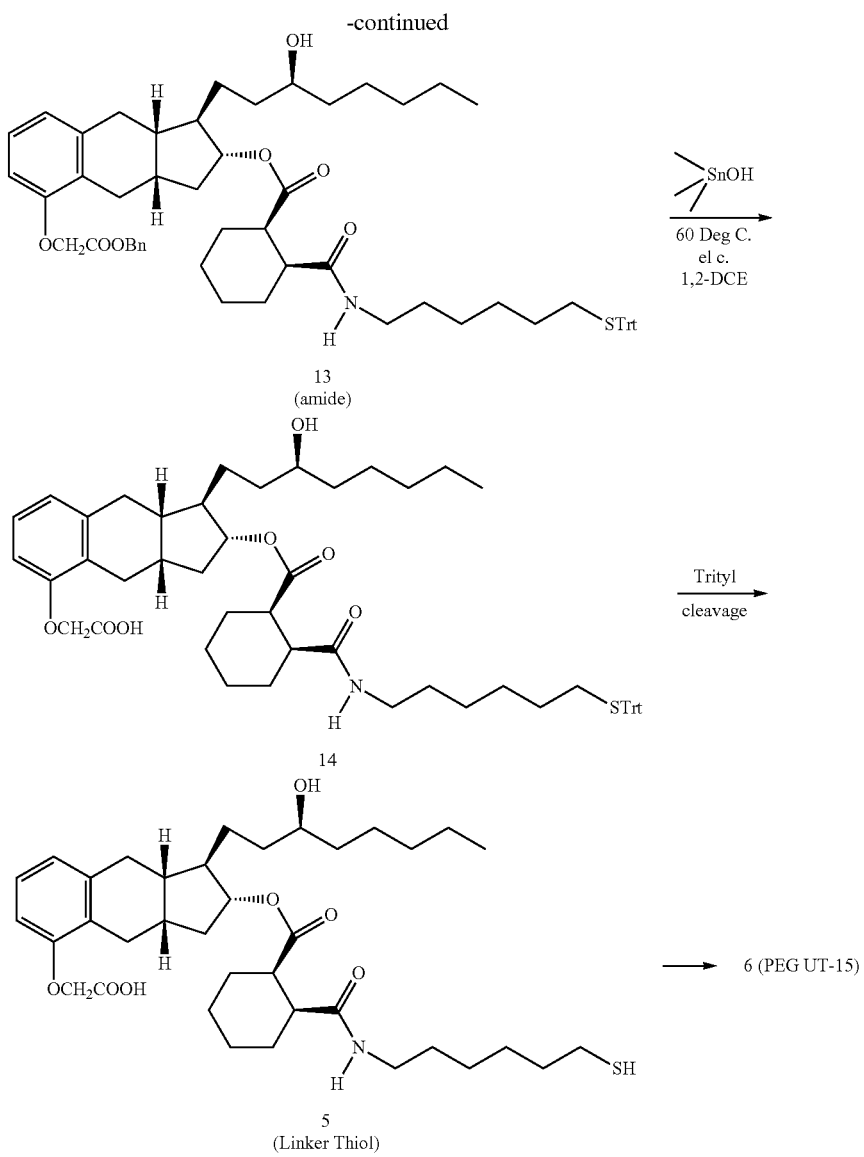

Step A: Coupling of Treprostinil Benzylester with Meso Anhydride (7→11)

To a suspension of cis-1,2-cyclohexanedicarboxylic anhydride (meso-anhydride) (7) (13.0 g) and quinine (9, 36.48 g) in anhydrous toluene (370 mL) was added slowly treprostinil benzyl ester (8a, 27.0 g) keeping the temperature of the mixture between 5-10° C. under argon. The reaction mixture was mechanically stirred at ambient temperature overnight. After ~18 h, the reaction mixture was treated with 1N hydrochloric acid (150 mL). The organic layer was separated and washed with brine (1×50 mL), dried over sodium sulfate (Na$_2$SO$_4$), filtered and concentrated in vacuo to give acid intermediate (11). The crude product was purified by flash chromatography on silica gel using 5-100% Ethyl Acetate (EtOAc) in hexanes. Fractions containing the desired compound were collected and reduced under vacuo to yield pure acid (11, 26.4 g). The acid intermediate (5.4 g) was subjected to quinine salt formation (10) using stoichiometric amount of quinine and crystallized using mixture of isopropyl alcohol and heptanes to obtain quinine salt (10, 5.4 g). A small amount of the quinine salt (10) so obtained was neutralized with 1N hydrochloric acid to give analytical sample of acid intermediate with high chiral purity (11; chiral purity 99% by HPLC). The acid intermediate was optionally purified via salt formation and neutralization methodology.

Step B: Coupling of Amine with Acid (11→13)

A 250-mL round-bottom flask equipped with a magnetic stirrer and stir bar was charged with a solution of acid intermediate (11) (11.6 g) in dichloromethane (120 mL). To this solution diisopropylethyl amine (9.4 g) and amine side chain (12, 7.90 g) were added at room temperature followed by EDCI (4.2 g) and HOBt (2.98 g). The reaction mixture was stirred at ambient until completion of the reaction. Progress of the reaction was monitored by TLC. After approximately 1-2 h reaction mixture was quenched with water (200 mL) and stirred for 5-10 min. At this stage organic layer was extracted, washed with brine (50 mL), dried over Na$_2$SO$_4$, filtered and concentrated in vacuo to obtain crude amide intermediate (13). The crude product was purified by flash chromatography on silica gel using 5-25% EtOAc in hexanes. Fractions containing the desired compound were collected and reduced under vacuo to yield pure amide (14.6 g).

Step C: Hydrolysis of Benzyl Ester (13→>14)

A 250-mL round-bottom flask equipped with a magnetic stirrer and stir bar was charged with a solution of amide intermediate (13, 7.4 g) in 1,2-dichloroethane (80 mL). To this solution trimethyl tin hydroxide (4.7 g) was added at room temperature and reaction mixture heated to 55-60° C. The reaction mixture was stirred at 55-60° C. until completion of the reaction. Progress of the reaction was monitored by TLC. After approximately 4-5 h reaction mixture was quenched with water (100 mL) and stirred for 5-10 min. At this stage organic layer was extracted, washed with brine (50 mL), dried over $Na_2SO_4$, filtered and concentrated in vacuo to obtain crude acid intermediate (14). The crude product was purified by flash chromatography on silica gel using 5-100% EtOAc in hexanes. Fractions containing the desired acid product were collected and reduced under vacuo to yield pure acid (5.4 g).

Step D: Cleavage of Trityl Group to Obtain Linker Thiol (14→5)

A 50-mL round-bottom flask equipped with a magnetic stirrer and stir bar was charged with a solution of acid intermediate (14, 0.95 g) in hexafluoroisopropanol (HFIPA) (10 mL). To this solution was added triethylsilane (TES) (1.0 mL) followed by trifluoroacetic acid (TFA) (1.0 mL) were added at room temperature and the reaction mixture was stirred at ambient until completion of the reaction. Progress of the reaction was monitored by HPLC. After approximately 15-30 min. reaction mixture was quenched with water (3×20 mL) and stirred for 5-10 min. At this stage organic layer was extracted, washed with brine (10 mL), dried over $Na_2SO_4$, filtered and concentrated in vacuo to obtain crude linker thiol (5, 1.2 g). The crude product (5) was purified by flash chromatography on silica gel using 20-100% EtOAc in hexanes. Fractions containing the desired linker thiol product (5) were collected and reduced under vacuo to yield pure linker thiol (5, 0.53 g, chiral purity 99%, chemical purity 94.02%).

Step E: PEGylation (5→6)

A 500-mL round-bottom flask equipped with a magnetic stirrer and stir bar was charged with 4 arm 20 k Da PEG (1.43 g) this was dissolved in 1:9 $MeCN/H_2O$ (50 mL) until complete dissolution (about 5 min). Treprostinil linker thiol 5 (0.208 g, 4.4 eq.) was added to the PEG solution at ambient (dissolved in 120 ml of $MeCN/H_2O$ 9:1). The reaction was started by the addition of phosphate buffer (pH 6.5, 15 ml, the pH was checked by pH paper). After ~3 h HPLC of the reaction mixture showed completion of reaction. Reaction mixture was diluted with dichloromethane (DCM) (130 ml) and 5% aqueous citric acid (100 mL). The aqueous phase was extracted with dichloromethane (2×40 mL). The combined organic layers were washed with a mixture of water/saturated NaCl 1:1 (100 mL). At this stage organic layers were combined, dried over $Na_2SO_4$, filtered and concentrated in vacuo at ambient to 8-10 ml volume. This was cooled to −20° C. and tert-butyl methyl ether (MTBE) (150 mL) added in 2-3 portions at −20° C. and the slurry was stirred at −20° C. for 20 min, filtered and the cake was rinsed with cold MTBE (30-40 mL). The white solid was dried in vacuo at RT to obtain PEG-UT15 (6, 1.43 g, 91% pure by HPLC).

Example 2

Stereospecific/Enatioselective Synthesis of Pegylated Prostacyclin Derivatives Via Chiral Hemiesters

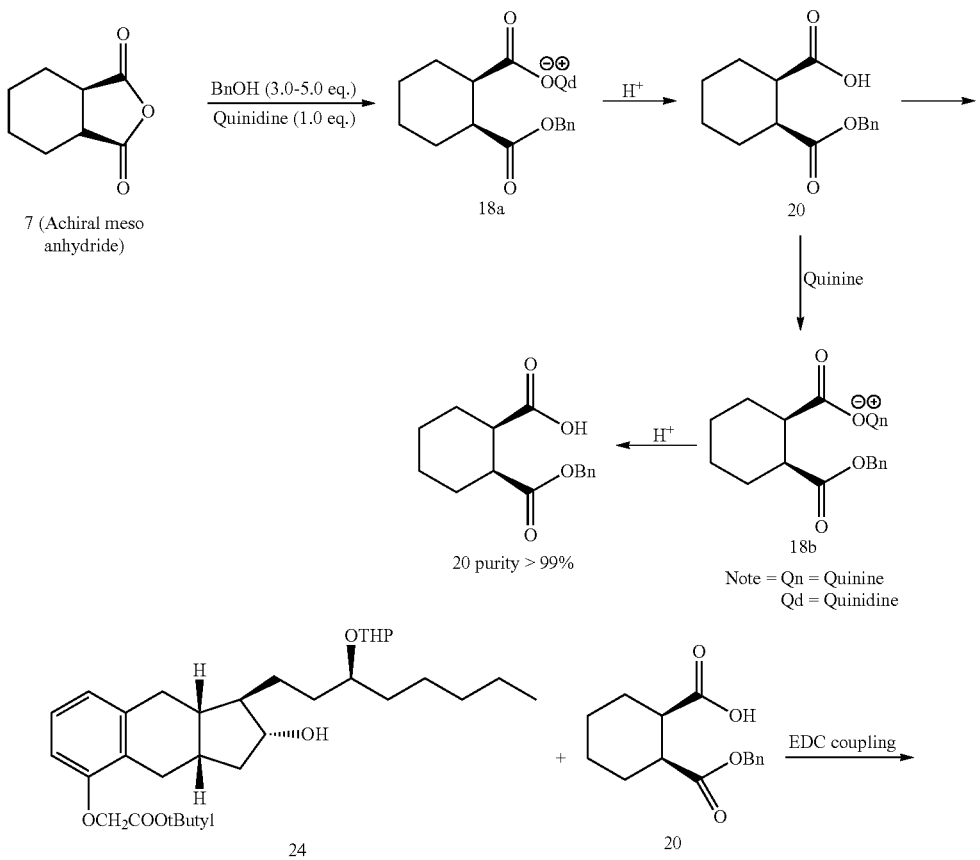

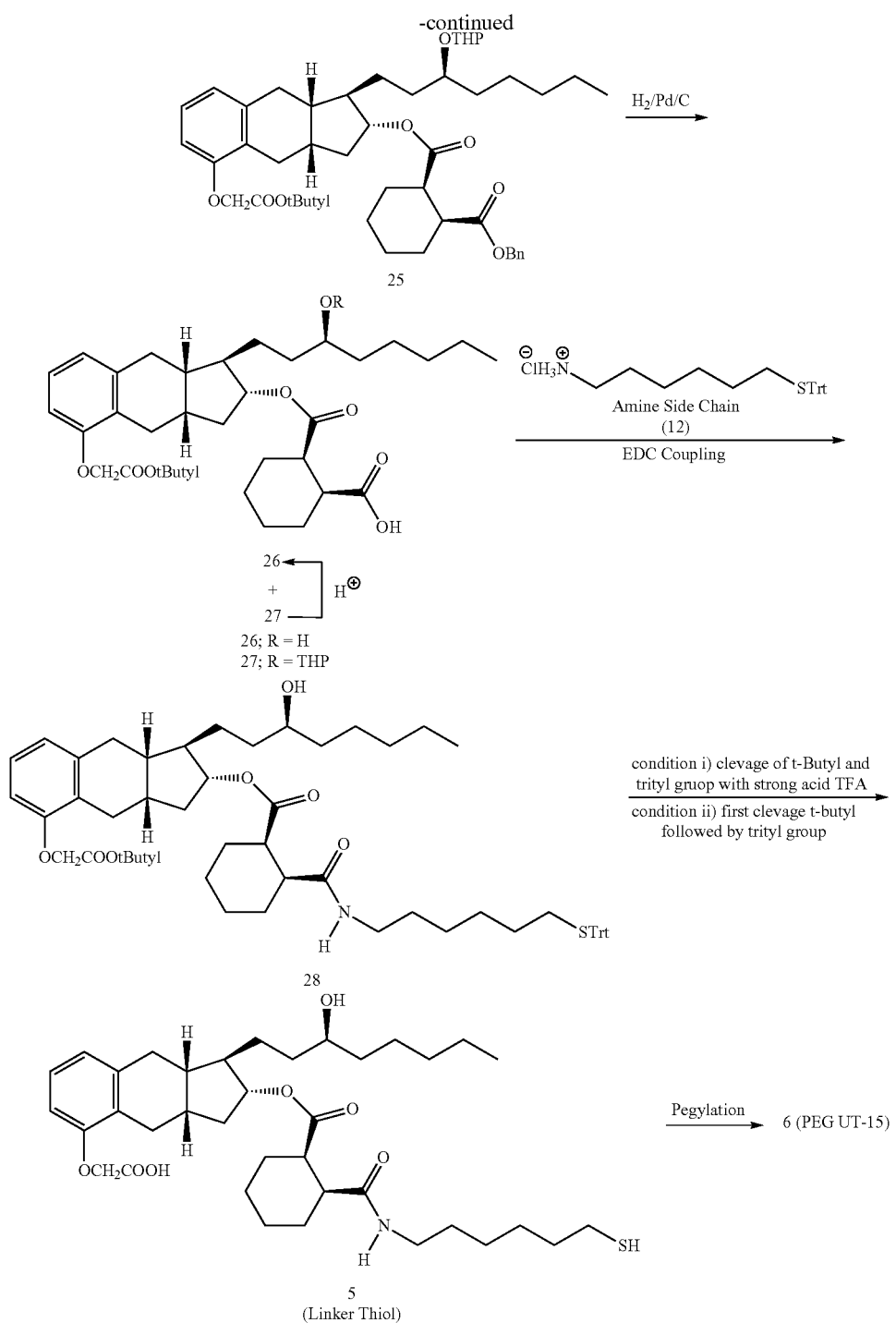

Step A: Preparation of Benzyl Hemiester (7→20)

To a suspension of cis-1,2-cyclohexanedicarboxylic anhydride (meso-anhydride) (7) (39.52 g, 256.36 mmol, 1.0 eq) and quinidine (91.48 g, 281.98 mmol, 1.10 eq) in anhydrous toluene (600 mL) was added slowly benzyl alcohol (83.17 g, 769.09 mmol, 3.0 eq) keeping the temperature of the mixture between 20-25° C. under argon (slightly exothermic reaction). The reaction mixture was mechanically stirred at ambient temperature overnight. After 24 h, the reaction mixture was checked by TLC (EtOAc/Hexanes, 3:7) and there was no meso-anhydride left. Then the mixture was treated with tert-butyl methyl ether (MTBE) (100 mL) and then acidified with 3 M hydrochloric acid (150 mL). The organic layer was separated and washed with 3M hydrochloric acid (1×50 mL), water (2×100 mL), brine (1×40 mL), dried ($Na_2SO_4$), filtered and concentrated in vacuo to give benzyl hemiester (20) and excess benzyl alcohol as viscous liquid (115.18 g) (chiral purity, 91.32% by chiral HPLC). This crude hemiester (115.18 g calculated as 60.52 g of available desired 20 based on 90% chemical purity, 230.74 mmol, 1.0 eq) was dissolved in acetone (550 mL) and then added quinine (74.86 g, 230.75 mmol, 1.0 eq) under argon at ambient temperature. The lightbrown clear solution was gently heated to reflux and during this time solid quinine salt of benzyl hemiester (18b) was formed. The mixture was heated to reflux for 1 h to dissolve the salt. Since the salt was soluble, more acetone was added until a clear solution was obtained. The total volume of acetone was 850 mL. To this clear solution was added hexane (1700 mL, twice the volume of acetone used) slowly at 56° C. with stirring and then the mixture was cooled to ambient temperature and stirred overnight. After 18 h, the quinine salt (18b) was collected in a Buchner funnel and washed the solid with hexane (2×100 mL), transfer the solid in a glass tray for air drying. The weight of the dried quinine salt (18b) was 116.25 g (86.0%) (chiral purity, 99.76% by chiral HPLC).

Under similar reaction condition, two more lots of quinine salts of benzyl hemiester (18b) were prepared with 99.5% chiral purity and these three lots of quinine salts of benzyl hemiester (18b) were combined (total 374.90 g) and transferred into a 5-L three-necked flask fitted with mechanical stirrer. To the quinine salt was added water (1000 mL) and tert-butyl methyl ether (MTBE) (2000 mL) and to the suspension was added slowly 1.0M hydrochloric acid (1000 mL) with stirring. The mixture was stirred at ambient temperature for 1 h. The organic layer was separated and washed with 1.0M hydrochloric acid (2×500 mL), water (2×500 mL), brine (1×100 mL), dried ($Na_2SO_4$), filtered and concentrated in vacuo give viscous translucent liquid of benzyl hemiester (20) (166.4 g, 99.2% chiral purity by HPLC). Benzyl hemiester (19) was synthesized following similar experimental procedure.

Step B: Coupling of Hemister with t-Boc Etser of Treprostinil (20→25)

A 50-mL, two-necked, round-bottom flask equipped with a magnetic stirrer and stir bar was charged with a solution of chiral benzyl hemiester (20, 0.182 g) in dichloromethane (10 mL) under argon. To this clear solution EDCI (0.480 g) and DMAP (0.305 g) were added while stirring. The stirring was continued for 10-15 min. To this mixture t-Boc ester of treprostinil (24, 0.350 g) was added and reaction mixture was stirred at ambient temperature for approximately 5-6 h. The reaction mixture was washed with water (10 mL), organic layer extracted, washed with brine (10 mL), dried over sodium sulfate and concentrated in vacuo to obtain the crude coupled product (25). The crude product was purified by column chromatography using 230-400 mesh silica gel and eluted with a gradient solvent of ethyl acetate in hexanes (0-10%). The fractions containing the desired compound were evaporated in vacuo to yield pure (25) as a colorless, viscous liquid (0.400 g) which was carried over for subsequent step.

Step C: Hydrogenolysis of Benzyl Ester (25→26)

A 100-mL round-bottom flask equipped with a magnetic stirrer and stir bar was charged with a solution of coupled benzyl ester product (2.3 g) in methanol (40 mL). To this solution, Pd/C (0.500 g, 50% wet) was added while stirring at room temperature. The reaction mixture was evacuated and pressurized with hydrogen gas using balloon. The reaction mixture was hydrogenated at balloon pressure overnight (~16 h) at ambient temperature. After 16 h the reaction was monitored by TLC. At this stage the reaction mixture was filtered through a pad of Celite (~4 g). The Celite pad was washed with methanol (~50 mL). The combined filtrates were evaporated in vacuo to get crude acid product (26) and crude product was purified by column chromatography using 250-400 mesh silica gel. A solvent gradient of ethyl acetate in hexanes (5-100%) was used to elute the product from column. The fractions containing desired product were evaporated in vacuo to yield pure acid (26, 1.63 g).

Step D: Coupling of Amine with Acid (26→28)

A 100-mL round-bottom flask equipped with a magnetic stirrer and stir bar was charged with a solution of acid intermediate (26, 0.750 g) in dichloromethane (10 mL). To this solution diisopropylethyl amine (0.566 g) and amine side chain (12, 0.539 g) were added at room temperature followed by EDCI (0.288 g) and HOBt (0.202 g). The reaction mixture was stirred at ambient until completion of the reaction. Progress of the reaction was monitored by TLC. After approximately 1-2 h reaction mixture was quenched with water (20 mL) and stirred for 5-10 min. At this stage organic layer was extracted, washed with brine (10 mL), dried over $Na_2SO_4$, filtered and concentrated in vacuo to obtain crude amide intermediate (28). The crude product was purified by flash chromatography on silica gel using 5-25% EtOAc in hexanes. Fractions containing the desired compound were collected and reduced under vacuo to yield pure amide (28, 0.78 g).

Step E: Cleavage of t-Boc and Trityl Groups (28→5)

A 50-mL round-bottom flask equipped with a magnetic stirrer and stir bar was charged with a solution of intermediate 28 (0.075 g) in hexafluoroisopropanol (HFIPA) (2.5 mL). To this solution was added triethylsilane (TES) (0.15 mL) followed by trifluoro acetic acid (TFA) (0.15 mL) were added at room temperature and the reaction mixture was stirred at ambient until completion of the reaction. Progress of the reaction was monitored by HPLC. After approximately 6-7 h. reaction mixture was quenched with water (3×20 mL) and stirred for 5-10 min. At this stage organic layer was extracted, washed with brine (10 mL), dried over $Na_2SO_4$, filtered and concentrated in vacuo to obtain crude linker thiol (5). The crude product (5) was purified by flash chromatography on silica gel using 20-100% EtOAc in hexanes. Fractions containing the desired linker thiol product (5) were collected and reduced under vacuo to yield pure linker thiol (5, 0.030 g, chiral purity 97%).

The other isomer of linker thiol (47) can be synthesized starting from the other isomer of benzyl hemiester (19), using the experimental procedure describe above.

Step F: PEGylation (5→6)

A 500-mL round-bottom flask equipped with a magnetic stirrer and stir bar was charged with 4 arm 20 k Da PEG (1.43 g) this was dissolved in 1:9 MeCN/$H_2O$ (50 mL) until complete dissolution (about 5 min). Treprostinil linker thiol 5 (0.208 g, 4.4 eq.) was added to the PEG solution at ambient (dissolved in 120 ml of MeCN/H2O 9:1). The reaction was started by the addition of phosphate buffer (pH 6.5, 15 ml, the pH was checked by pH paper). After ~3 h HPLC of the reaction mixture showed completion of reaction. Reaction mixture was diluted with DCM (130 ml) and 5% aqueous citric acid (100 mL). The aqueous phase was extracted with dichloromethane (2×40 mL). The combined organic fractions were washed with a mixture of water/saturated NaCl 1:1 (100 mL). At this stage organic layers combined, dried over $Na_2SO_4$, filtered and concentrated in vacuo at ambient to 8-10 ml volume. This was cooled to −20° C. and MTBE (150 mL) added in 2-3 portions at −20° C. and the slurry was stirred at −20° C. for 20 min, filtered and the cake was rinsed with cold MTBE (30-40 mL). The white solid was dried in vacuo at RT to obtain PEG-UT15 (6, 1.43 g, 91% pure by HPLC).

Example 3

Stereospecific/Enatioselective Synthesis of Pegylated Prostacyclin Derivatives Via Diastereomeric Salt Crystallization of Hemiesters

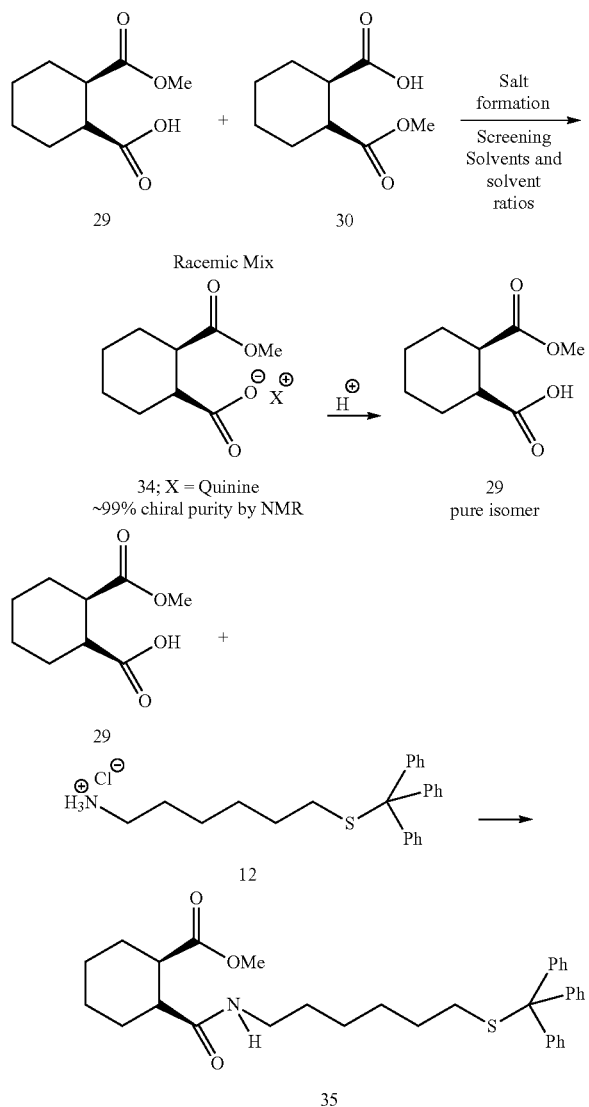

Step A: Synthesis of Racemic Methyl Hemiester (7→29, 30)

Meso-anhydride (7) was refluxed in MeOH (10 vol. w/v) to obtain racemic mix of hemiesters (29 and 20). Racemic mixture of 29 and 30 (12.08 g) was treated with quinine (21.28 g) in acetone (225 ml) at 55-60° C. and stirred for 30 min. To this clear solution hexane was added (650 ml) and cooled to rt. while stirring for 3 hr. At this stage white solid crashed out of solution. This was filtered and dried to obtain 22 g of the quinine salt (34). The quinine salt was characterized by NMR.

1 g of quinine salt (34) was taken in acetone (20 ml) and heated at 55-60° C. to obtain clear solution and this was cooled to RT while stirring overnight. White solid so obtained was filtered and dried to obtain 490 mg of pure quinine salt of acid isomer 29. The salt was neutralized with 1N HCl to obtain free acid (29) with high chiral purity (99%).

Step B: Synthesis of Racemic Methyl Hemiester (29→35)

Coupling with amine was carried in using experimental procedure described in Examples 1 and 2. Alternatively, the coupling can be performed by activating the acid with thionyl chloride instead with EDCI.

Example 4

Synthesis of Amine Side Chain

Synthesis of Trifluoroacetaminohexyl Iodide (42, R=COCF$_3$)

To a solution of triphenylphosphonine (1.35 g, 0.0052 mol, 2.2 eq) in dichloromethane (15 mL) was added iodine (1.31 g, 0.0052 mol, 2.2 eq) under argon at ambient temperature. The mixture was stirred for 10 min and then imidazole (0.35 g, 0.0052 mol, 2.2 eq) and stirred for 10 min followed by a solution of trifluoroacetaminohexanol (41, R=COCF$_3$) (500 mg, 0.0023 mol, 1.0 eq) in dichloromethane (15 mL). The reaction mixture was gently refluxed for 2 h. The reaction mixture was monitored by TLC (EtOAc/Hexane, 1:4). After completion of the reaction, the mixture was treated with hexane (30 mL). The mixture was passed through a pad of silica gel using a mixture of EtOAc/Hexane (1:4) to give pure iodo compound (42, R=COCF$_3$) (710 mg).

Synthesis of Trifluoroacetaminohexyl Trityl Thioether (43)

Method A

To a solution of trifluoroacetaminohexyl iodide (42, R=COCF$_3$) (285 mg, 0.0088 mol, 1.0 eq) in acetonitrile (25 mL) were added powdered potassium carbonate (304 mg, 0.0220 mol, 2.5 eq) and trityl thiol (243 mg, 0.0088 mol, 1.0 eq) under argon at ambient temperature. The reaction mixture was stirred at ambient temperature overnight and monitored by aTLC (EtOAc/Hexane, 1:9). After 20 h, the reaction mixture was treated with hexane (15 mL) and passed through a pad of silica gel and the filtrate was concentrated in vacuo to give trifluoroacetaminohexyl trityl thioether (43) (425 mg).

Synthesis of Trifluoroacetaminohexyl Trityl Thioether (43)

Method B

To a solution of trifluoroacetaminohexyl iodide (42, R=COCF$_3$) (400 mg, 0.0124 mol, 1.0 eq) in DMF (12 mL) were added DBU (207 mg, 0.0136 mol, 1.1 eq) and trityl thiol (342 mg, 0.0124 mol, 1.0 eq) under argon at ambient temperature. The reaction mixture was stirred at ambient temperature overnight and monitored by TLC (EtOAc/Hexane, 1:9). After 20 hr, the reaction mixture was treated with ethyl acetate and washed with saturated ammonium chloride solution (2×), brine, dried (Na$_2$SO$_4$), filtered and concentrated in vacuo to give trifluoroacetaminohexyl trityl thioether (43) (560 mg).

Synthesis of Aminohexyl Trityl Thioether Hydrochloride Salt (12)

To a solution of trifluoroacetaminohexyl trityl thioether (43) (115 mg, 0.00024 mol, 1.0 eq) in methanol/water (9:1) (15 mL) was added potassium carbonate (0.051 mg. 0.00036 mol, 1.5 eq) at ambient temperature. The reaction mixture was stirred at 40° C. The reaction was monitored by TLC (EtOAc/Hexane, 1:4). After completion of the reaction, methanol from the mixture was evaporated in vacuo and the residue was treated with water and ethyl acetate. The organic layer was separated and washed with brine, dries (Na$_2$SO$_4$), filtered and concentrated in vacuo to give aminohexyl trityl thioether (12) (80 mg). The compound 12 was treated with a solution of hydrogen chloride in dioxane followed by filtration to obtain aminohexyl trityl thioether hydrochloride salt (12) as solid (90 mg).

Scheme 12 summarizes one embodiment the process of preparation of pegylated treprostinil.

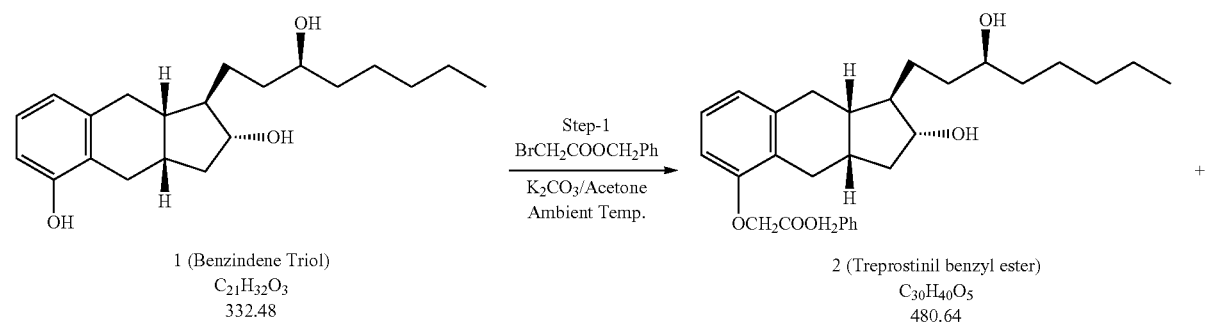

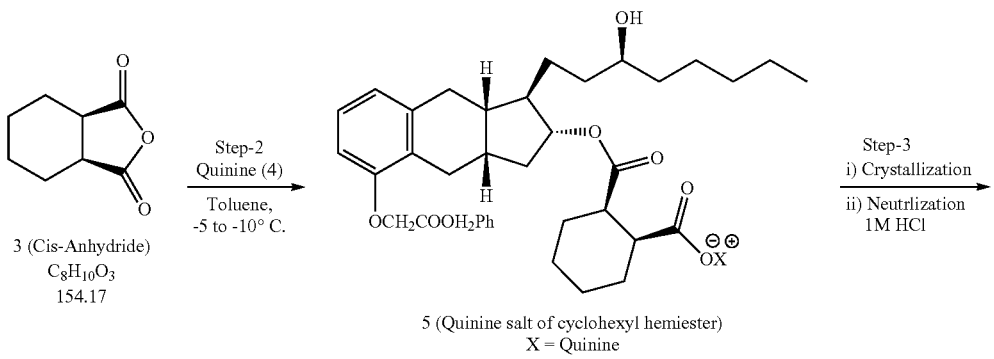

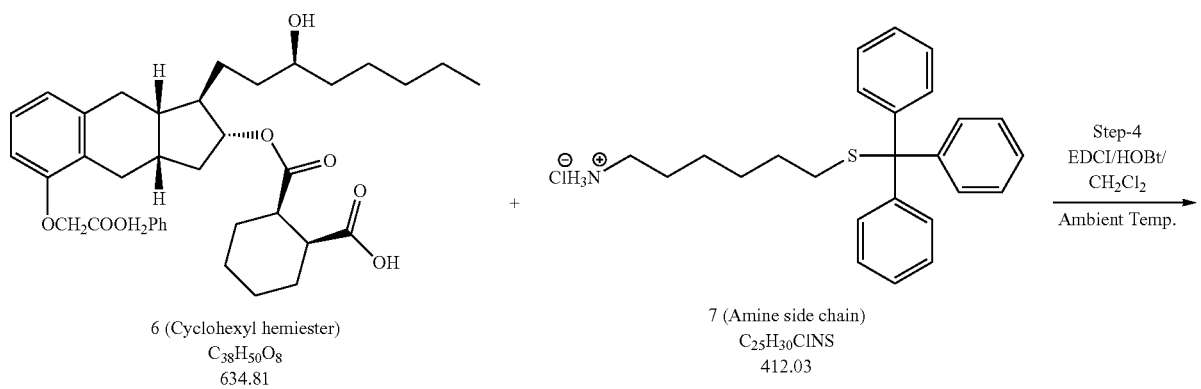

-continued
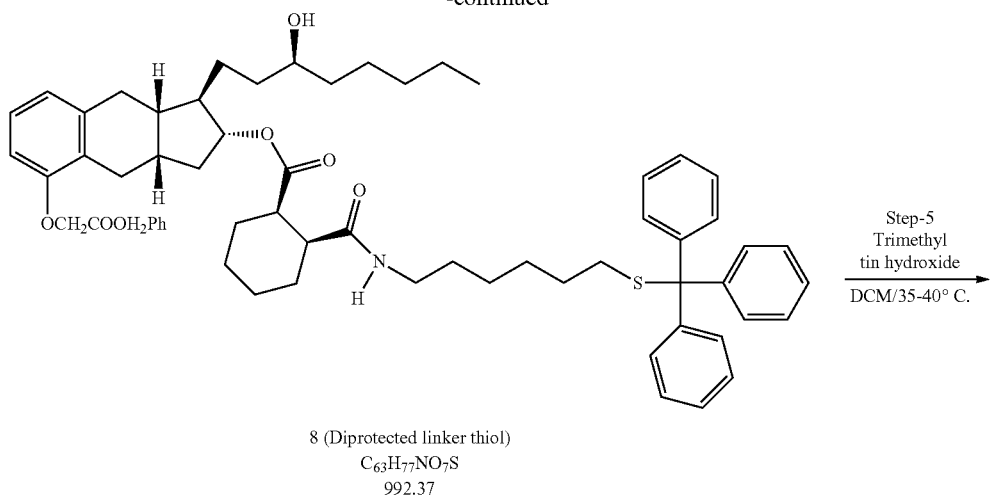
8 (Diprotected linker thiol)
C₆₃H₇₇NO₇S
992.37
Step-5
Trimethyl tin hydroxide
DCM/35-40° C.
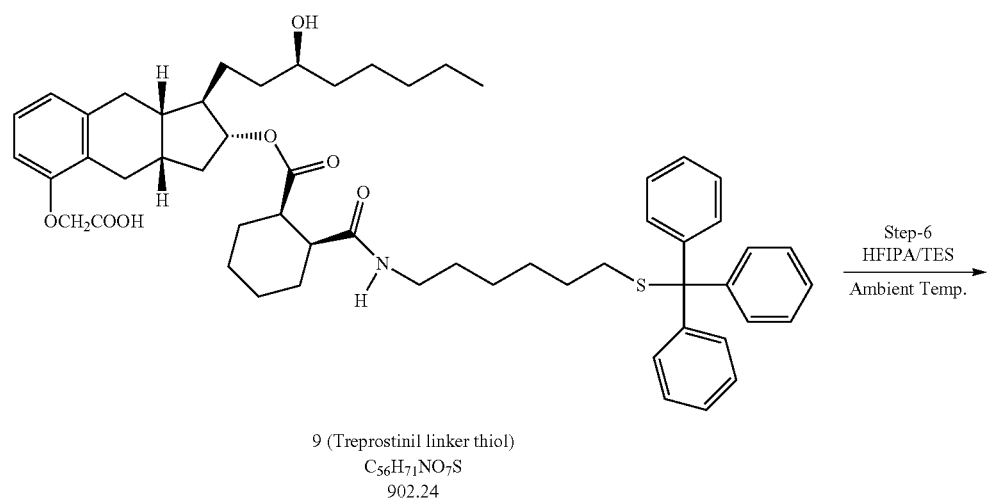
9 (Treprostinil linker thiol)
C₅₆H₇₁NO₇S
902.24
Step-6
HFIPA/TES
Ambient Temp.
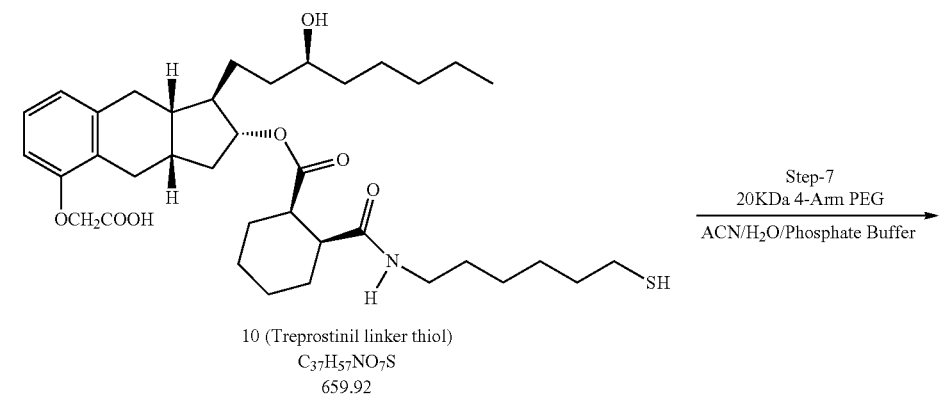
10 (Treprostinil linker thiol)
C₃₇H₅₇NO₇S
659.92
Step-7
20KDa 4-Arm PEG
ACN/H₂O/Phosphate Buffer

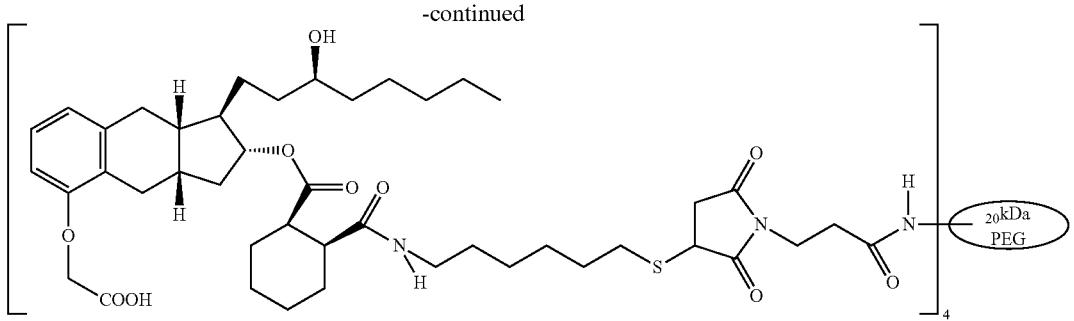

11 (TransCon PEG treprostinil or TCP treprostinil)

Experimental

Step-1

Synthesis of Treprostinil Benzyl Ester (2) from Triol (1)

A 50-L jacketed reactor equipped with a mechanical stirrer and temperature probe was charged a solution of benzindene triol (1) (1.0 kg) in acetone (12.0 L). To this solution was added powdered potassium carbonate (935.0 g) followed by benzyl bromoacetate (828.0 g) at ambient temperature. The reaction mixture was stirred at ambient temperature until completion of the reaction. Progress of the reaction mixture was monitored by tlc (MeOH/CH$_2$Cl$_2$, 1:9) and reaction was found to be complete after 32 h. The reaction mixture was filtered and filter cake was washed with acetone (6.0 L). The filtrate was concentrated in vacuo to get treprostinil benzyl ester (2) as light yellow color viscous liquid. The crude product was agitated in mixture of hexanes (5.0 L) and ethyl acetate (0.15 L) to obtain granular solid. This solid was filtered and dried in vacuo to obtain free flowing, off-white solid benzyl ester (1.36 kg, 94.5%).

Step 2 & 3

Coupling of Treprostinil Benzyl Ester (2) with Cis-Anhydride (3) & Crystallization Of Quinine Salt (5)

A 50-L jacketed reactor equipped with a mechanical stirrer and temperature probe was charged with benzyl ester (2) (300.0 g) in toluene (3.95 L). To this solution, quinine (4) (286.0 g) was added and this reaction mixture was cooled to −5 to −10° C. while stirring. Then cis-1,2-cyclohexanedicarboxylic anhydride (3) (92.31 g) was added while keeping the temperature of the reaction mixture between −5° C. to −10° C. under argon. The reaction mixture was mechanically stirred at −5° C. to −10° C. for 3-5 h. Progress of the reaction was monitored by UPLC at regular intervals of 1 h. After ~4-5 h, the reaction was found to be complete and the reaction mixture was treated with 1N hydrochloric acid (2.18 L) while keeping the temperature between 0° C. to 10° C. The organic layer was separated and aqueous phase was extracted with ethyl acetate (3.0 L). The combined organic layers were washed twice with water (2×5.0 L), separated and concentrated in vacuo to yield crude acid intermediate (681.0 g). The crude product was purified by flash chromatography on silica gel using 5-100% EtOAc in hexanes. Fractions containing the desired compound were collected and reduced under vacuo to yield pure acid (181.0 g). The acid intermediate (181.0 g) was subjected to quinine salt formation (5) using stoichiometric amount of quinine and crystallized using mixture of acetone and hexanes to obtain quinine salt (5) (177.0 g). The quinine salt (5) so obtained was neutralized with 1M hydrochloric acid (0.63 L) to give chirally pure cyclohexyl hemiester (6) (117.45 g; 30%) with chiral purity (>99%).

Step 4

Coupling of Cyclohexyl Hemiester (6) with Amine Side Chain (7)

A 50-L jacketed reactor equipped with a mechanical stirrer and temperature probe was charged with a solution of cyclohexyl hemiester (6) (115.0 g) in dichloromethane (2.5 L). To this solution amine side chain (7) (77.77 g) was added followed by HOBt (29.40 g) at ambient temperature. To this reaction mixture, EDCI (42.25 g) and diisopropylethylamine (58.93 g) were added under argon. The reaction mixture was stirred at ambient temperature until completion of the reaction. Progress of the reaction was monitored by TLC. After approximately 3-4 h reaction mixture was quenched with water (1.5 L) and stirred for 5-10 minutes. At this stage, the organic layer was extracted, and aqueous phase extracted again with dichloromethane (2.0 L). The combined organic layers were washed twice with water (1×2.0 L and 1×1.5 L), separated and concentrated in vacuo at 40±5° C. to obtain crude amide intermediate (8) (204.0 g). The crude product was purified by flash chromatography on silica gel using 0-45% EtOAc in hexanes. Fractions containing the desired compound were collected and concentrated in vacuo to yield pure diprotected linker thiol (8) (163.11 g; 90.7%).

Step 5

Hydrolysis of Diprotected Linker Thiol (8) with Trimethyl Tin Hydroxide

A 50-L jacketed reactor equipped with a stirrer and temperature probe was charged with a solution of diprotected linker thiol (8) (161.0 g) in dichloromethane (2.0 L). To this solution trimethyl tin hydroxide (123.28 g) was added at ambient temperature and reaction mixture was heated to 35-40° C. The reaction mixture was stirred at 35-40° C. until completion of the reaction. Progress of the reaction was monitored by TLC. After 8-9 h reaction mixture was cooled to 15-20° C. and quenched with water (2.0 L) and stirred for 5-10 minutes. At this stage organic layer was extracted and washed with water (3×3.0 L) and concentrated in vacuo to obtain crude acid intermediate (9) (292.0 g). The crude product was purified by flash chromatography on silica gel using 5-100% EtOAc in hexanes and later with 5-20% methanol in dichloromethane. Fractions containing the desired product were collected and concentrated in vacuo at 40±5° C. to yield pure trityl protected linker thiol (9) (140.0 g, 95.6%).

Step 6

Cleavage of Trityl Group of (9) to Obtain Treprostinil Linker Thiol (10)

A 50-L jacketed reactor equipped with a mechanical stirrer and temperature probe was charged with a solution of trityl protected linker thiol (9) (138.0 g) in hexafluoroisopropanol (HFIPA) (1.5 L). To this solution was added triethylsilane (TES) (0.15 L) and the reaction mixture was stirred at ambient temperature until completion of the reaction. Progress of the reaction was monitored by UPLC. After 3-4 h reaction mixture was quenched with water (1×2.0 L) and dichloromethane (2.0 L) was added while stirring. At this stage, the organic layer was separated and the aqueous phase was extracted with dichloromethane (4.0 L). The combined organic layers were washed with water (2×2.0 L) followed by brine (2.0 L), and the concentrated in vacuo at 30±5° C. to obtain crude linker thiol (10) (303.0 g). The crude product was purified by flash chromatography on silica gel using 20-100% EtOAc in hexanes and later with 5-20% methanol in dichloromethane. Fractions containing the desired linker thiol product (10) were collected and concentrated in vacuo to yield pure treprostinil linker thiol (10) (81.8 g, 81.1%).

Step 7

Pegylation of Treprostinil Linker Thiol (10) with 4-Arm 20 kDa PEG

A 100-L jacketed reactor equipped with a mechanical stirrer and a temperature probe was charged with 4-arm 20 kDa PEG (270.0 g) followed by mixture of $MeCN:H_2O$ (1:9) (7.1 L). This mixture was stirred at ambient temperature until complete dissolution. Treprostinil linker thiol (10) (41.0 g) was dissolved in a mixture of $MeCN:H_2O$ (9:1) (17.8 L) and was added to the above prepared 4-arm 20 kDa PEG solution at ambient temperature. At this stage phosphate buffer (2.8 L) was added to the reaction mixture (pH 7.5) and the reaction mixture was allowed to stir at ambient temperature until completion of the reaction. The progress of the reaction was monitored by UPLC by taking an aliquot from reaction mixture after every 1 h. After ~4 h UPLC of the reaction mixture showed completion of the reaction. The reaction mixture was quenched by addition of 5% citric acid solution (12.0 L), followed by addition of 5% brine (2.7 L) and dichloromethane (21.0 L). This mixture was allowed to stir for 15-20 minutes and then organic layer was separated. The aqueous phase was extracted with dichloromethane (2×5.0 L). The combined organic layers were washed with a mixture of water and brine (1:1) (6.0 L), dried over $Na_2SO_4$ (3.7 kg) and concentrated in vacuo at 25±3° C. to a total 1.8 L volume in a rotavap flask. This concentrated solution was filtered through a polypropylene filter cloth under vacuo and rotavap flask was rinsed with mixture of dichloromethane:acetonitrile (1:1) (2.4 L) and filtered through polypropylene filter cloth. The combined filtrates were transferred to a clean reactor and this solution was cooled to −25° C. To this solution, pre-cooled MTBE (21.5 L) was added and this mixture was stirred at −10 to −15° C. for 20-30 min. The white solid so obtained was filtered through Aurora filter using polypropylene filter cloth and the filter cake was washed with cold MTBE (11.0 L). The white solid was dried under compressed dried air (CDA) at ambient temperature to obtain TransCon PEG treprostinil (11) (TCP-UT15) (290.0 g, 73.7%).

Scheme 13 illustrates one embodiment of a process for synthesizing pegylated beraprost.

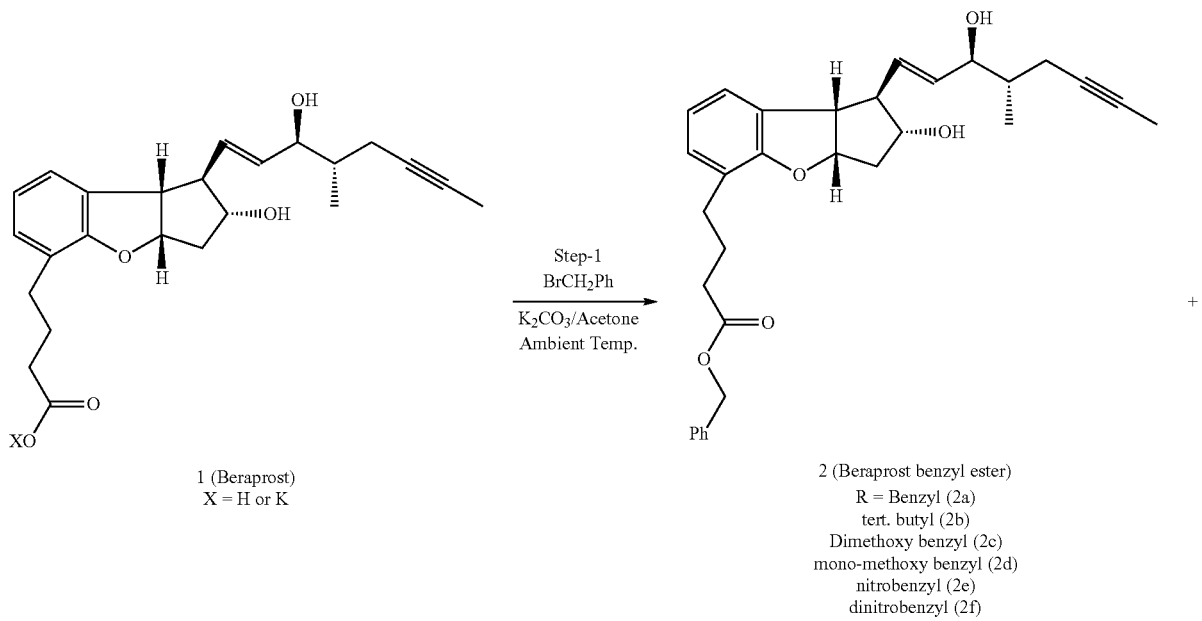

1 (Beraprost)
X = H or K 2 (Beraprost benzyl ester)
R = Benzyl (2a)
tert. butyl (2b)
Dimethoxy benzyl (2c)
mono-methoxy benzyl (2d)
nitrobenzyl (2e)
dinitrobenzyl (2f)

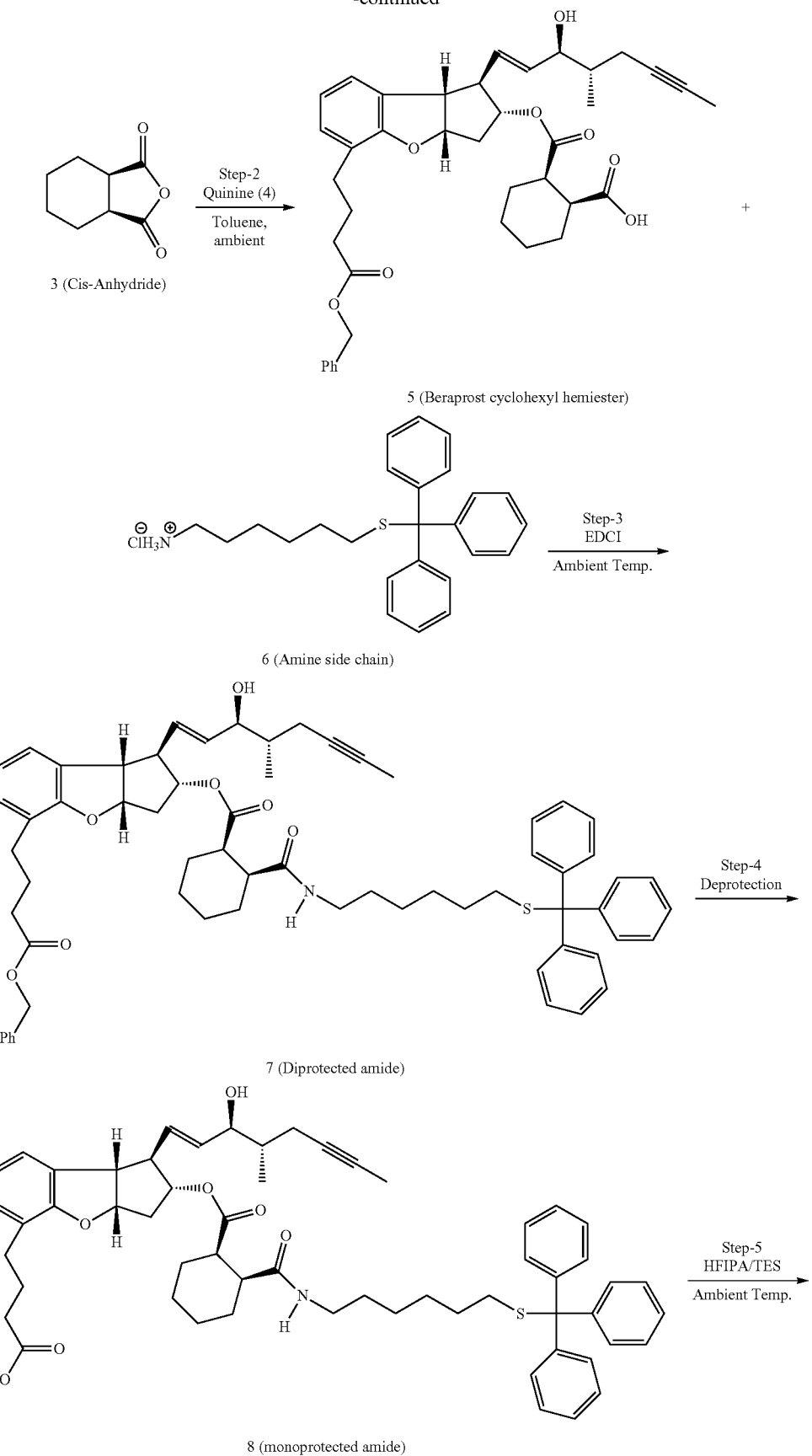

-continued

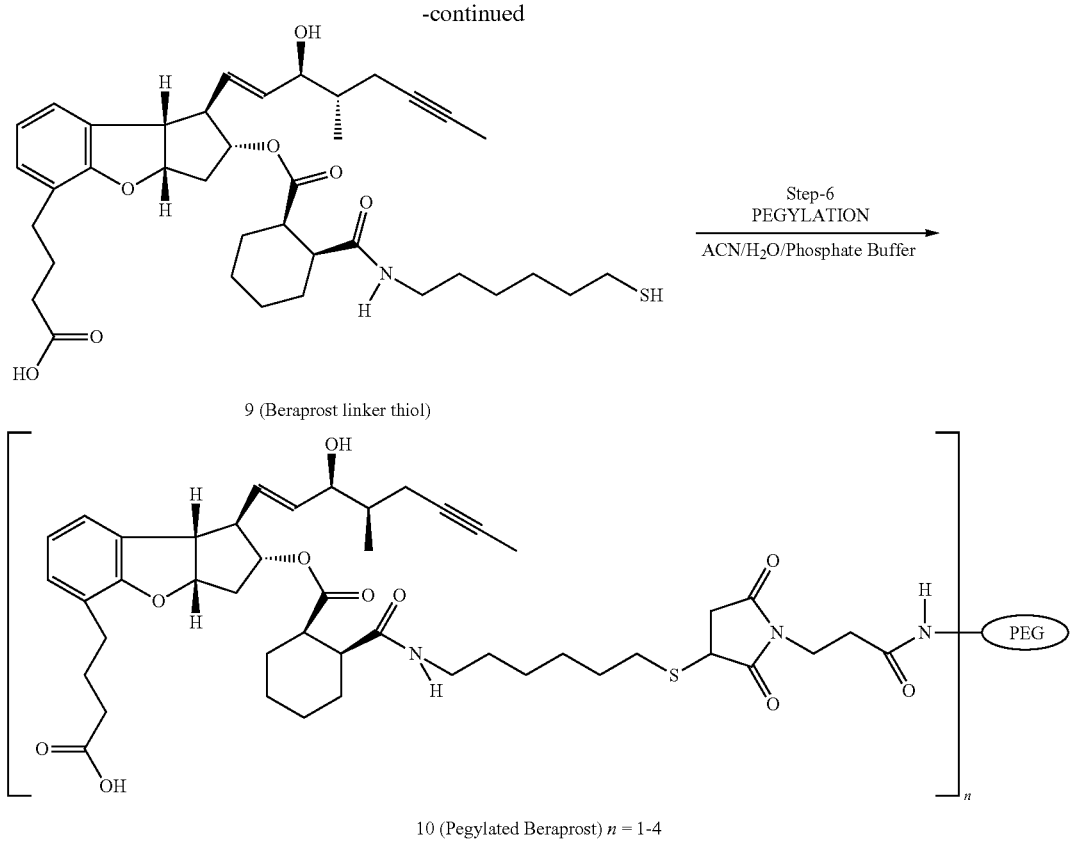

9 (Beraprost linker thiol)

10 (Pegylated Beraprost) n = 1-4

Step 1→2 (Beraprost Benzyl Ester Formation)

Lot # D-1117-194

To a solution of beraprost (free acid or salt form) (200 mg) in acetone (20 mL) was added dimethylamino pyridine (DMAP) (2 mg) and benzyl bromide (117 mg) at room temperature. This was stirred at room temperature to a clear solution. To this solution tetrabutylammonium iodide (50 mg) was added and the reaction mixture was stirred at reflux temperature for 2 h. After 2 h, the reaction mixture was checked by tlc (MeOH/$CH_2Cl_2$, 1:9) and reaction was found to be complete. The reaction mixture was evaporated on vacuo to obtain crude oil. This was treated with 1N hydrochloric acid (~5 mL) and EtOAc (10 mL) and stirred for 10 minutes. The organic layer was separated and washed with brine (10 mL), dried over $Na_2SO_4$, filtered and concentrated in vacuo to give crude ester intermediate (2). The crude product (2) was purified by flash chromatography on silica gel using EtOAc followed by 10% MeOH in $CH_2Cl_2$ to elute the product. Fractions containing the desired compound were collected and reduced under vacuo to yield pure beraprost benzyl ester (2) (222 mg). $^1$H NMR showed the formation of the desired compound.

Step 2→3 (Coupling of Beraprost Benzyl Ester with Meso Anhydride)

Lot # D-1124-029

To a solution of compound 2 (220 mg) in toluene (7 mL) was added quinine (191 mg) followed by cis-1,2-cyclohexanedicarboxylic anhydride (meso-anhydride) (62 mg). The reaction mixture was stirred at ambient temperature overnight. After ~18 h, the crude reaction mixture was loaded on a pad of silica gel and was purified by flash chromatography on using 0-100% EtOAc in hexanes. Fractions containing the desired compound were collected and reduced under vacuo to yield pure acid (3) (110 mg). $^1$H NMR showed the formation of the desired compound.

Step 3→4 (Coupling of Amine with Acid)

Lot # D-1117-201

A 25-mL round-bottom flask equipped with a magnetic stirrer and stir bar was charged with a solution of acid intermediate (3) (86 mg) in dichloromethane (7 mL). To this solution, amine side chain (6) (60 mg), EDCI (33 mg) and HOBt (23 mg) were added at room temperature, followed by diisopropylethylamine (45 mg). The reaction mixture was stirred at ambient until completion of the reaction. Progress of the reaction was monitored by TLC. After approximately 1-2 h reaction mixture was quenched with water (10 mL) and stirred for 5-10 mins. At this stage organic layer was washed with brine (10 mL), dried over $Na_2SO_4$, filtered and concentrated in vacuo to obtain crude amide intermediate (4). The crude product was purified by flash chromatography on silica gel using 5-40% EtOAc in hexanes. Fractions containing the desired compound were collected and reduced under vacuo to yield pure amide (42 mg). $^1$H NMR showed the formation of the desired compound.

Step 4→5 (Hydrolysis of Benzyl Ester)

Lot # D-1124-032

To a solution of amide intermediate (4) (40 mg) in 1,2-dichloroethane (5 mL), trimethyltin hydroxide (25 mg) was added at room temperature and reaction mixture heated to 65-70° C. The reaction mixture was stirred at 65-70° C. until completion of the reaction. Progress of the reaction was monitored by TLC. After approximately 11 h, TLC of the reaction mixture showed very little product and at this stage extra trimethyltin hydroxide (50 mg) was added and reaction mixture stirred at 65-70° C. for another 5 hrs. At this stage TLC the reaction mixture showed approximately 40-50% product along with unreacted starting material. The reaction mixture was quenched with water (10 mL) and stirred for 5-10 mins. At this stage organic layer was extracted, washed with brine (5 mL), dried over $Na_2SO_4$, filtered and concentrated in vacuo to obtain crude acid intermediate (5). The crude product was purified by flash chromatography on silica gel using 0-100% EtOAc in hexanes followed by 10% MeOH in $CH_2Cl_2$ to elute the product. Fractions containing the pure product were collected and reduced under vacuo to yield pure compound (20 mg).

Pegylated prostacyclin derivatives, such as pegylated treprostinil and pegylated beraprost, may be used, in a pharmaceutical formulation for treating a number of conditions by administering to a subject, such as a human being in need thereof. For example, pegylated treprostinil may be used for treating a condition, for which treprostinil is known to be effective. Similarly, pegylated beraprost may be used for treating a condition, for which beraprost is known to be effective. Conditions, for which treprostinil is known to be effective, include but not limited to pulmonary hypertension (including primary and secondary pulmonary hypertension and pulmonary arterial hypertension), peripheral vascular disease, severe intermittent claudication, critical limb ischemia, ischemic lesions, asthma, pulmonary fibrosis, diabetic neuropathic foot ulcers, interstitial lung disease. Conditions, for which beraporst is known to be effective, include, but not limited to pulmonary hypertension, vascular disease.

A pharmaceutical formulation may comprise a pegylated prostacyclin derivative, such as pegylated treprostinil and pegylated beraprost, and a pharmaceutically acceptable carrier or excipient.

The term "pharmaceutical" when used herein as an adjective means substantially non-deleterious to the recipient mammal. By "pharmaceutical formulation" it is meant the carrier, diluent, excipients and active ingredient(s) must be compatible with the other ingredients of the formulation, and not deleterious to the recipient thereof.

A pegylated prostacyclin derivative, such as pegylated treprostinil and pegylated beraprost, can be formulated prior to administration. The selection of the formulation should be decided by the attending physician taking into consideration the same factors involved with determining the effective amount.

Liquid dosage forms for oral administration of a pegylated prostacyclin derivative, such as pegylated treprostinil and pegylated beraprost, include solutions, emulsions, suspensions, syrups and elixirs, which may be formulated prior to administration.

The total active ingredients in such formulations comprises from 0.1% to 99.9% by weight of the formulation. A pegylated prostacyclin derivative, such as pegylated treprostinil and pegylated beraprost, can be formulated with one or more additional active ingredients or as the sole active ingredient.

Pharmaceutical formulations of the present invention are prepared by procedures known in the art using well known and readily available ingredients. For example, a pegylated prostacyclin derivative, such as pegylated treprostinil and pegylated beraprost, either alone, or in combination with other active ingredient(s) are formulated with common excipients, diluents, or carriers, and formed into tablets, capsules, suspensions, solutions, injectables, aerosols, powders, and the like.

Pharmaceutical formulations of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral formulations may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, a pegylated prostacyclin derivative, such as pegylated treprostinil and pegylated beraprost, is mixed with at least one inert, pharmaceutical carrier such as sodium citrate, or dicalcium phosphate, and/or (a) fillers or extenders such as starches, sugars including lactose and glucose, mannitol, and silicic acid, (b) binding agents such as carboxymethyl-cellulose and other cellulose derivatives, alginates, gelatin, poly(vinylpyrrolidine), sucrose and acacia, (c) humectants such as glycerol, (d) disintegrating agents such as agar-agar, calcium carbonate, sodium bicarbonate, potato or tapioca starch, alginic acid, silicates and sodium carbonate, (e) moisturizing agents such as glycerol; (f) solution retarding agents such as paraffin, (g) absorption accelerating agents such as quaternary ammonium compounds, (h) wetting agents such as cetyl alcohol and glycerin monostearate, (i) absorbents such as kaolin and bentonite clay, and (j) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid formulations of a similar type may also comprise the fill in soft or hard gelatin capsules using excipients such as lactose as well as high molecular weight poly(ethylene glycols) and the like. Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract. The active ingredient(s) may also be microencapsulated in a sustained-release coating, with the microcapsules being made part of a pill of capsule formulation.

Liquid dosage forms for oral administration of a pegylated prostacyclin derivative, such as pegylated treprostinil and pegylated beraprost, include solutions, emulsions, suspensions, syrups and elixirs, which may be formulated from the particular polymorphic form prior to administration. In addition to the active components, liquid formulations may include inert diluents commonly used in the art such as water or other pharmaceutical solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof. Besides inert diluents, the liquid oral formulations may also include adjuvants such as wetting agents, emulsifying and suspending agents, and sweetening, flavoring, and perfuming agents. Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for the preparation of a compound of Formula I, or a pharmaceutically acceptable salt thereof:

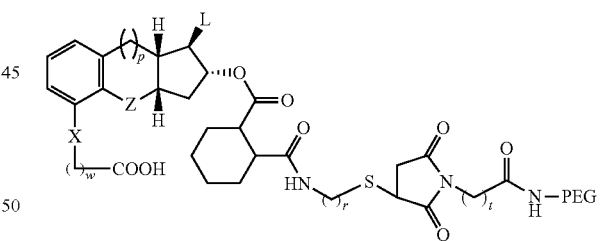

the process comprising:

coupling a meso anhydride of Formula III with an ester compound of Formula IV in the presence of a chiral ligand, to provide a compound of Formula V:

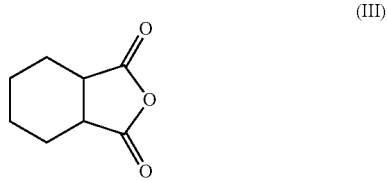 [SMILES: O=C1OC(=O)C2CCCCC12]

(IV)

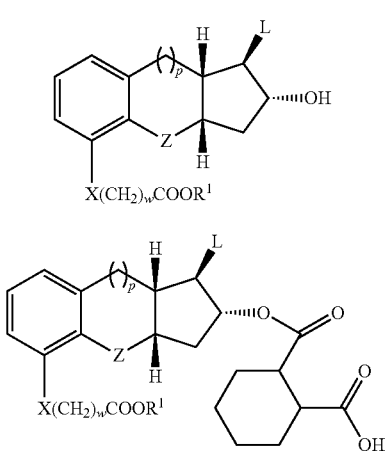

coupling the compound of Formula V with a compound of Formula VI to form a thiol, hydrolyzing the thiol with a hydrolyzing agent to form a compound of Formula VIII;

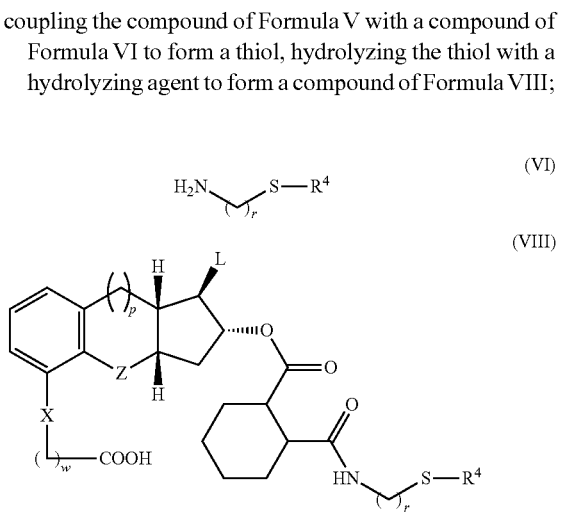

deprotecting the compound of Formula VIII to form the compound of Formula II:

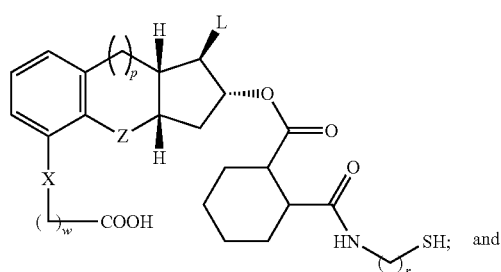

coupling the compound of Formula II with a PEG-maleimide compound to form the compound of Formula I;

wherein

X is O or $CH_2$;

Z is O or $CH_2$;

L is

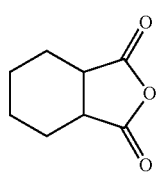

p=0 or 1;
r=1-8;
t=1, 2 or 3;
w=1, 2, or 3;
PEG is a polyethylene glycol moiety;
$R^1$ represents an acid protective group; and
$R^4$ represents a thiol protecting group.

2. The process of claim 1, wherein $R^1$ is a benzyl, tertiary-butyl, dimethoxy benzyl, nitrobenzyl or a dinitrobenzyl group.

3. The process of claim 1, wherein the chiral ligand is a quinine or quinidine derivative.

4. The process of claim 3, wherein the quinine or quinidine derivative is hydroquinine anthraquinone-1,4-diyl diether ((DHQ)$_2$AQN), hydroquinidine anthraquinone-1,4-diyl diether ((DHQD)$_2$AQN).

5. The process of claim 1, wherein the hydrolyzing agent is trimethyltin hydroxide.

6. The process of claim 1, wherein the compound of Formula VIII is deprotected using an acid.

7. The process of claim 6, wherein the acid is trifluoroacetic acid.

8. A process for the preparation of a compound of Formula I, or a pharmaceutically acceptable salt thereof:

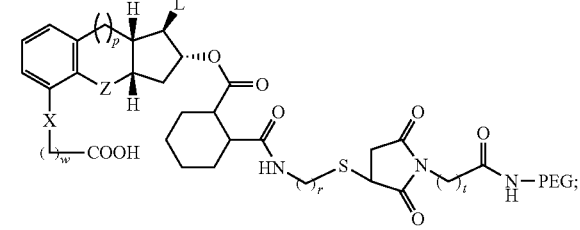

the process comprising: desymmeterizing a meso anhydride of structure III using an alcohol to provide an hemiester of Formula IX:

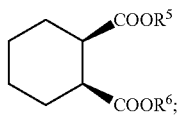

coupling the compound of Formula IX with a compound of Formula X,

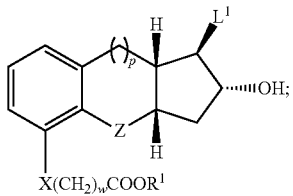
(X)

deprotecting the product of the coupling of Formula IX with Formula X, to form the compound of Formula XI:

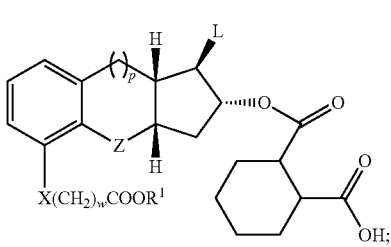
(XI)

coupling the compound of Formula XI with a compound of Formula VI, to obtain a compound of Formula VII:

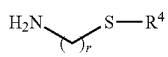
(VI)

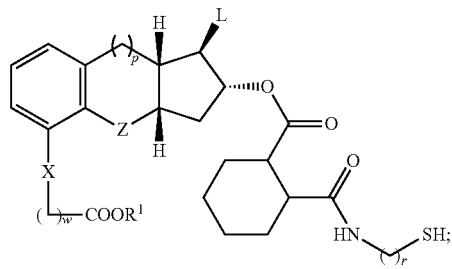
(VII)

deprotecting the compound of Formula VII to form the compound of Formula II:

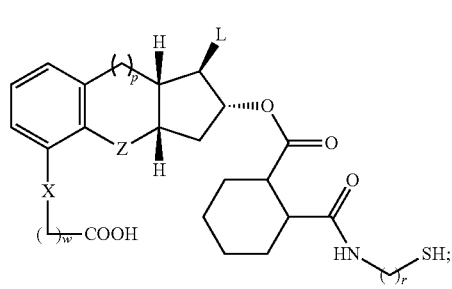
(II)

coupling the compound of Formula II with a polyethylene glycol maleimide compound to form the compound of Formula I;

wherein
X is O or $CH_2$;
Z is O or $CH_2$;
L is

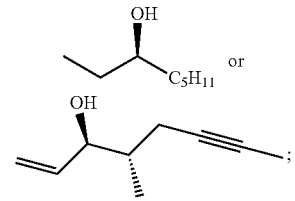

$L^1$ is

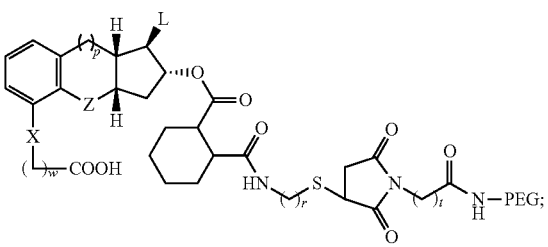

p=0 or 1;
r=1-8;
w=1, 2, or 3;
t=1, 2 or 3;
$R^1$ represents an acid protective group;
$R^2$ represents a hydroxyl protective group;
$R^4$ represents a thiol protecting group; and
one of $R^5$ and $R^6$ represents H and the other represents a $C_{1-6}$ alkyl, allyl, or an aryl group.

9. The process of claim 8, wherein $R^1$ is a benzyl, tertiary-butyl, dimethoxy benzyl, nitrobenzyl or a dinitrobenzyl group.

10. The process of claim 8, wherein $R^2$ is a tetrahydropyranyl, benzyl, methoxybenzyl, nitrobenzyl, tertiary butyl dimethyl silyl or a tertiary methyl dimethyl silyl group.

11. The process of claim 8, wherein the compound of Formula VII is deprotected using an acid.

12. The process of claim 11, wherein the acid is trifluoroacetic acid.

13. A process for the preparation of a compound of Formula I, or a pharmaceutically acceptable salt thereof (I)

the process comprising desymmeterizing a meso anhydride of Formula III using an alcohol to provide an hemiester of Formula IX:

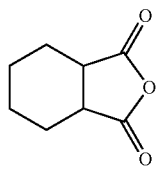
(III)

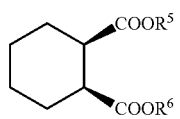
(IX)

coupling the compound of Formula IX with a compound of Formula VI, to provide a compound of Formula XII

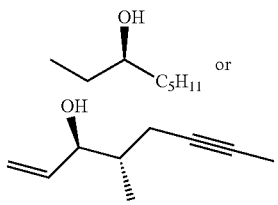
(VI)

(XII)
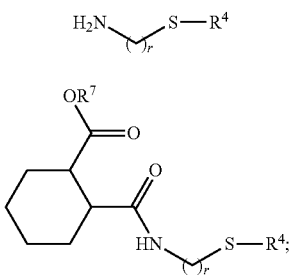

coupling the compound of Formula XII with a compound of Formula X,

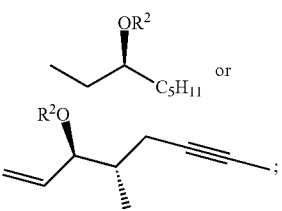
(X)

deprotecting the product of the coupling of Formula XII with Formula X, to form the compound of Formula II:

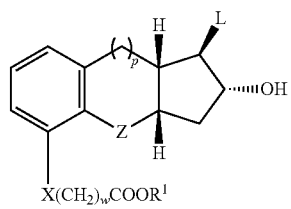
(II)

coupling the compound of Formula II with a polyethylene glycol maleimide compound to form the compound of Formula I;

wherein
X is O or $CH_2$;
Z is O or $CH_2$;
L is

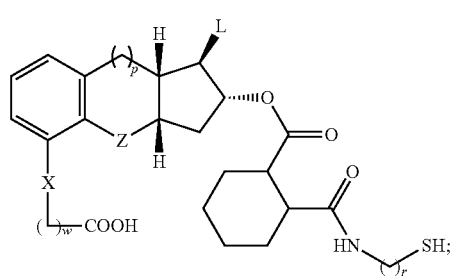

$L^1$ is $p=0$ or 1;
$r=1-8$;
$w=1, 2,$ or 3;
$t=1, 2$ or 3;
$R^1$ represents an acid protective group;
$R^2$ represents a hydroxyl protective group,
$R^4$ represents a thiol protecting group; and
one of $R^5$ and $R^6$ represents H and the other represents a $C_{1-6}$ alkyl, allyl, or an aryl group,
$R^7$ represents an acid protective group.

14. The process of claim 13, wherein $R^1$ is a benzyl, tertiary-butyl, dimethoxy benzyl, nitrobenzyl or a dinitrobenzyl group.

15. The process of claim 13, wherein $R^2$ is a tetrahydropyranyl, benzyl, methoxybenzyl, nitrobenzyl, tertiary butyl dimethyl silyl or a tertiary methyl dimethyl silyl group.

16. The process of claim 13, wherein $R^7$ is a $C_{1-6}$ alkyl group.

17. The process of claim 1, wherein the purity of compound of Formula I is at least 90%.

18. The process of claim 1, wherein the purity of compound of Formula II is at least 90%.

19. The process of claim 1, wherein the polyethylene glycol maleimide compound is a 4-arm 20 KDa PEG maleimide.

20. The process of claim 1, wherein X is O, w is 1, r is 6; and t is 2.

21. The process of claim 1, wherein X is $CH_2$, w is 2, r is 6; and t is 2.

22. A compound of Formula IB, prepared by the process of claim 1:

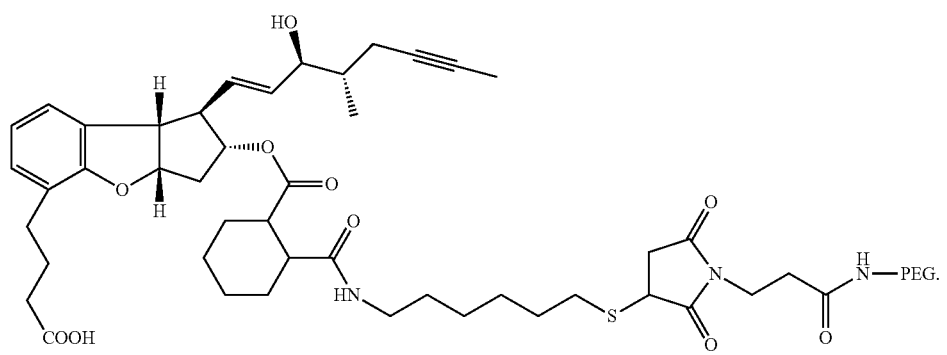
(IB)
23. A compound of Formula IIB, prepared by the process of claim 1:
(IIB)
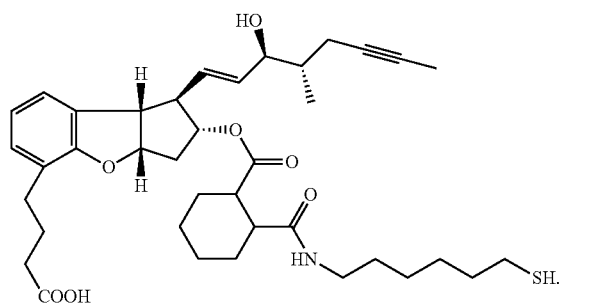
* * * * *